(12) United States Patent
Meissner, II et al.

(10) Patent No.: US 7,196,317 B1
(45) Date of Patent: Mar. 27, 2007

(54) SYSTEM, DEVICE, AND METHOD FOR DETECTING PERTURBATIONS

(75) Inventors: Kenith Meissner, II, College Station, TX (US); William B. Spillman, Jr., Floyd, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 144 days.

(21) Appl. No.: 11/090,898

(22) Filed: Mar. 25, 2005

(51) Int. Cl.
  *G01J 1/04* (2006.01)
(52) U.S. Cl. .................... 250/227.14; 385/13
(58) Field of Classification Search ........ 250/227.14, 250/227.15, 227.19; 385/13; 356/73.1
  See application file for complete search history.

(56) References Cited

U.S. PATENT DOCUMENTS

| | | | |
|---|---|---|---|
| 4,297,684 | A | 10/1981 | Butter |
| 4,843,233 | A | 6/1989 | Jeunhomme |
| 4,863,270 | A | 9/1989 | Spillman |
| 5,134,281 | A | 7/1992 | Bryenton |
| 5,212,379 | A | 5/1993 | Nafarrate |
| 5,291,013 | A | 3/1994 | Nafarrate |
| 5,436,444 | A | 7/1995 | Rawson |
| 6,498,652 | B1 | 12/2002 | Varshneya |
| 6,590,194 | B2 * | 7/2003 | Sardana et al. .......... 250/208.1 |
| 2003/0095263 | A1 | 5/2003 | Varshneya | |

OTHER PUBLICATIONS

W. B. Spillman et al., "Statistical-Mode Sensor for Fiber Optic Vibration Sensing Uses", Applied Optics, Aug. 1, 1989, pp. 3166-3176, vol. 28, No. 15.

W. B. Spillman et al., "Scaling and Antenna Gain in Integrating Fiber-Optic Sensors", Journal of Lightwave Technology, Jul. 1995, pp. 1222-1230, vol. 13, No. 7.

Dryer Huston et al., "Monitoring Micro Floor Vibrations with Distributed Fiber Optic Sensors", Part of SPIE Conference on Smart System for Bridges, Structures, and Highways, Mar. 1999, pp. 118-125, SPIE, vol. 3671.

* cited by examiner

*Primary Examiner*—Thanh X. Luu
(74) *Attorney, Agent, or Firm*—Michael Haynes PLC; Michael N. Haynes

(57) ABSTRACT

Certain exemplary embodiments comprise a system comprising a spatially distributed multimode optical fiber; a pixelated photodetector configured to detect a plurality of optical signals provided from said fiber, a first portion of the optical signals indicative of modal conversion and a second portion of the optical signals indicative of modal interference, a predetermined area of said pixelated photodetector adapted to be illuminated by the first portion of the optical signals; and a signal processing module adapted to decode and interpret a plurality of detected variables related to the optical signals.

42 Claims, 34 Drawing Sheets

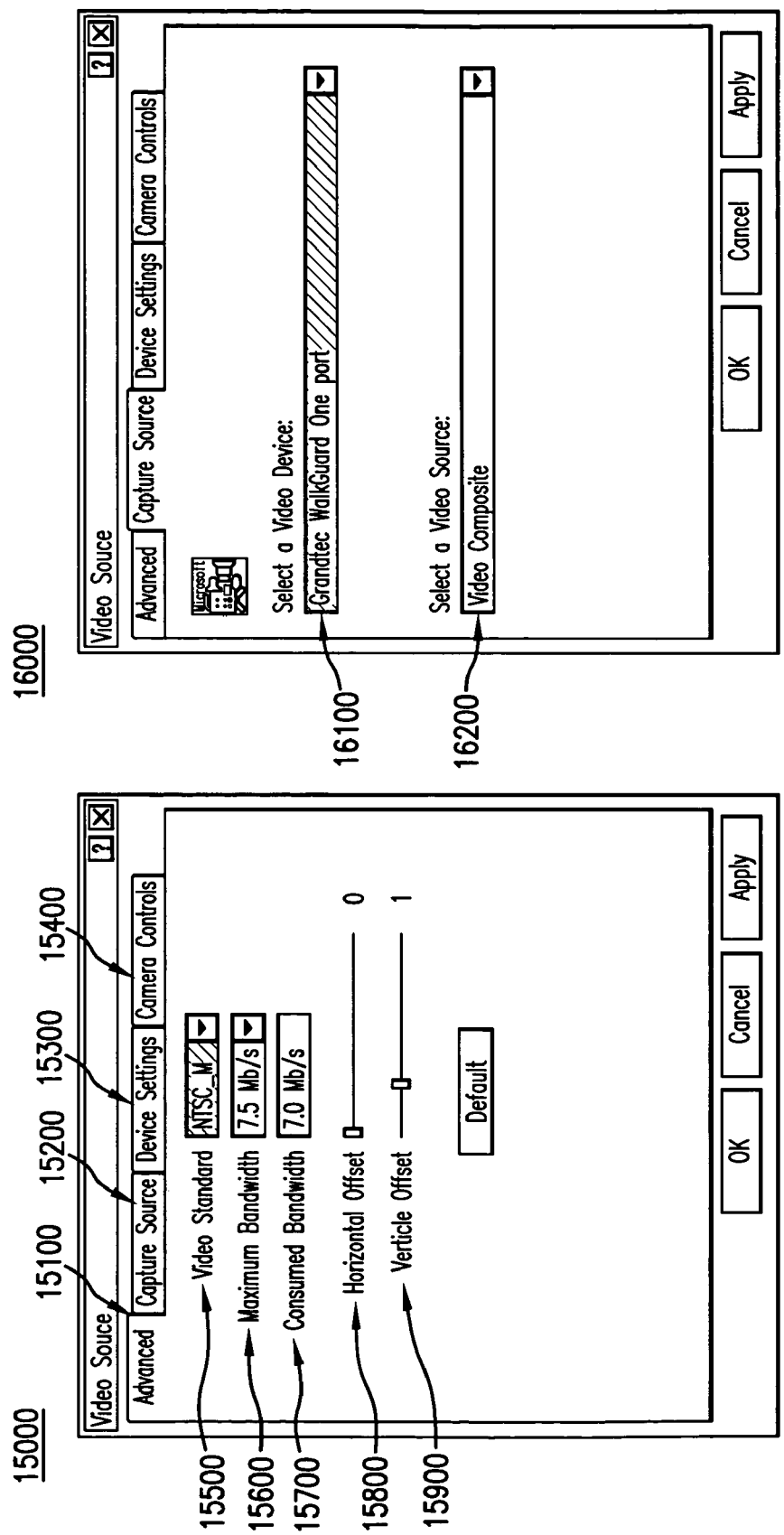

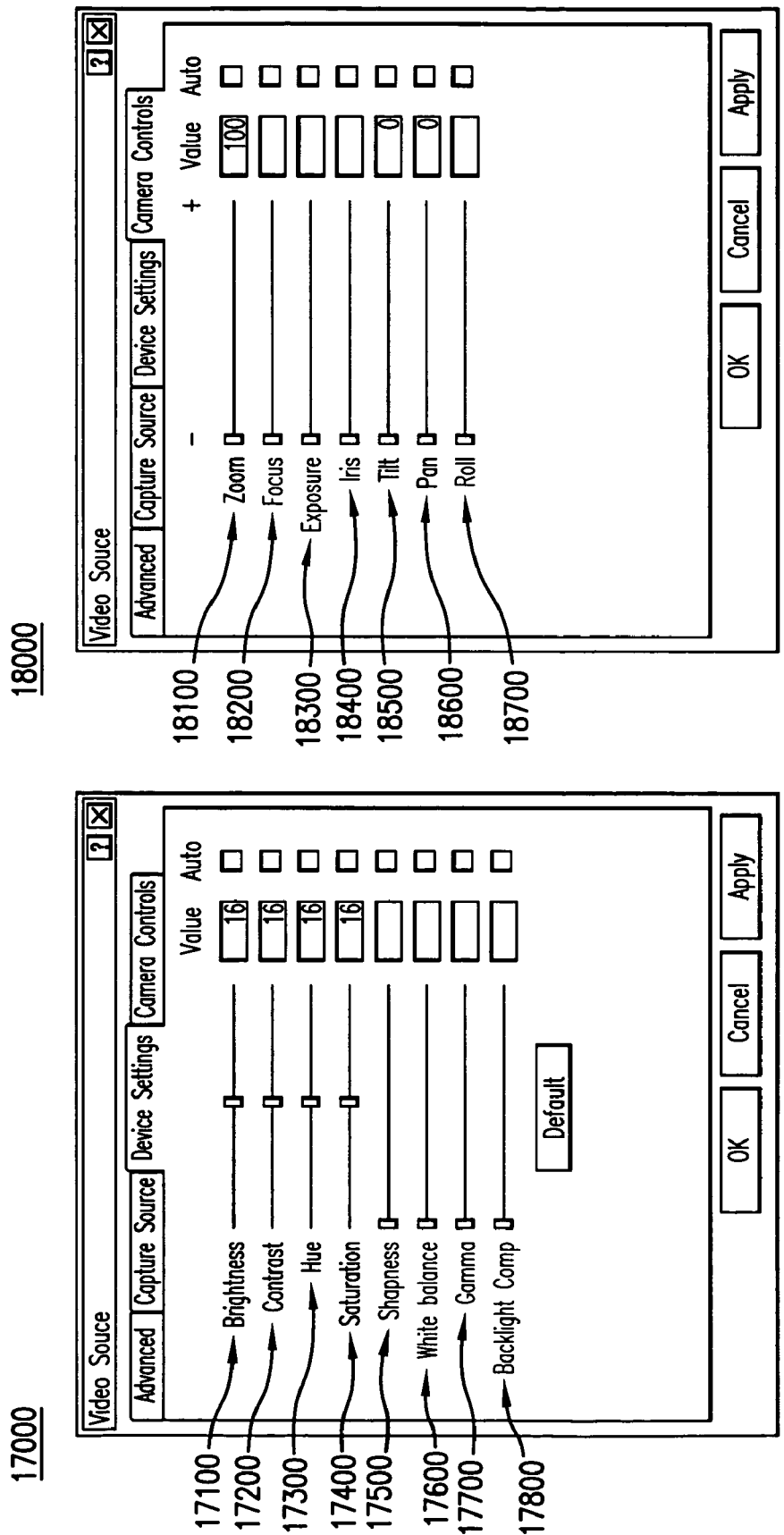

19000

SYSTEM, DEVICE, AND METHOD FOR DETECTING PERTURBATIONS

CROSS-REFERENCE TO RELATED APPLICATIONS

This application claims priority to, and incorporates by reference in its entirety, the following documents:
Pending U.S. Provisional Patent Application Ser. No. 60/556,383, filed 26 Mar. 2004; and
Pending International Patent Application Serial Number PCT/US03/36680, filed 17 Nov. 2003, which designates the United States of America.

BRIEF DESCRIPTION OF THE DRAWINGS

A wide array of potential embodiments can be better understood through the following detailed description and the accompanying drawings in which:

FIG. 15 is an exemplary user interface 15000;

FIG. 16 is an exemplary user interface 16000;

FIG. 17 is an exemplary user interface 17000;

FIG. 18 is an exemplary user interface 18000;

DEFINITIONS

Figure 1:
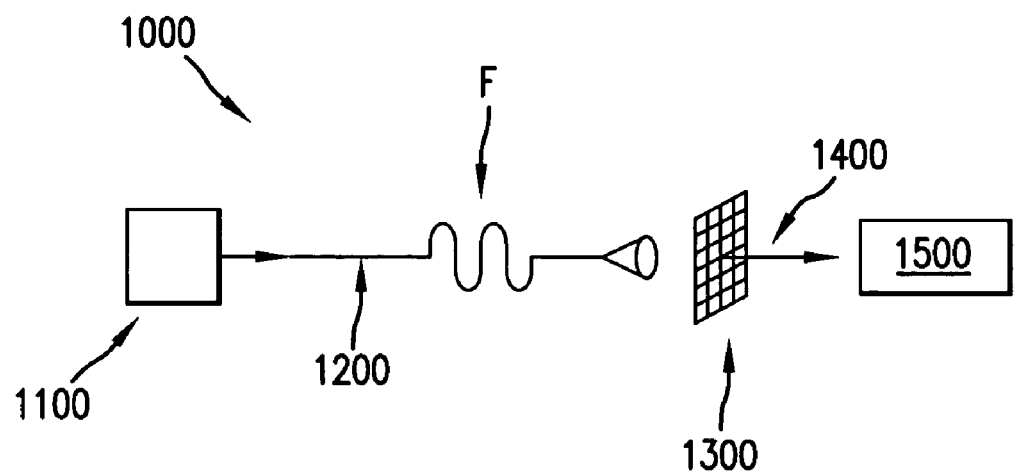
FIG. 1 is a block diagram of an exemplary embodiment of a multimode fiber optic sensor.

When the following terms are used herein, the accompanying definitions apply.

adapted—designed, constructed, placed, oriented, and/or operated.

annular area—a curvilinear region outside a central area of a thing and within and/or bounded by a perimeter of the thing.

applied—incident directly and/or indirectly upon.

central area—a curvilinear region within and offset from a perimeter of a thing.

charge-coupled device (CCD)—a light-sensitive integrated circuit that stores and displays the data for an image in such a way that each pixel (picture element) in the image is converted into an electrical charge the intensity of which is related to a color in the color spectrum (which can be a black-and-white continuum). For a system supporting, for example 65,535 colors, there will be a separate value for each color that can be stored and recovered. One of the two main types of image sensors used in digital cameras. When a picture is taken, the CCD is struck by light coming through the camera's lens. Each of the thousands or millions of tiny pixels that make up the CCD convert this light into electrons. The number of electrons, usually described as the pixel's accumulated charge, is measured, then converted to a digital value. This last step can occur outside the CCD, in a component called an analog-to-digital converter.

coherent—having waves with similar direction, amplitude, and phase that are capable of exhibiting interference.

complementary metal-oxide semiconductor (CMOS)—one of the two main types of image sensors used in digital cameras. Its basic function is the same as that of a CCD.

coupled—connected or linked by any known means, including mechanical, fluidic, acoustic, electrical, magnetic, optical, etc.

decode—to convert data by reversing the effect of previous encoding, and/or to interpret a code and/or signal.

detect—to receive and respond to a signal and/or stimulus.

digital camera—a camera that captures an image not on film, but in an electronic imaging sensor that takes the place of film.

encode—to convert data by the use of a code, frequently one consisting of binary numbers, in such a manner that reconversion to the original form is possible. Alternatively, to append redundant check symbols to a message for the purpose of generating an error detection and/or correction code.

fiber optic sensor—a device that utilizes an optical fiber as a transducer.

field emitter—a device that is fabricated on a sub-micron scale with lithography technique, and that emits electrons immediately when a voltage is applied.

high order mode—any mode other than the lowest order mode.

higher order mode—a mode having a higher angle of incidence with respect to the longitudinal axis of a fiber than a another, lower order, mode.

illuminated—at least partially lighted; characterized by light incident thereon.

image—an at least two-dimensional representation of an object and/or phenomenon.

integrated—formed or united into a whole or into another entity.

integrating—providing the sum or total of; additive.

interpret—to make sense of and/or assign a meaning to.

light pattern—a visible pattern, such as an interference pattern or speckle, created by combined modes of light.

lowest order mode—also known as the fundamental mode and the $LP_{01}$ mode, is the mode in which light passes through an optical fiber substantially parallel to the fiber's longitudinal axis.

matched spatial filtering—filtering a spatial pattern to emphasize a variable of interest.

modal conversion—a coupling of light from a high order guided azimuthal mode to a lower order, previously unexcited, guided azimuthal mode.

modal interference—a variation of received amplitude due to mode self-interaction and/or mode—mode interaction.

mode—in a waveguide or cavity, one of the various possible patterns of propagating or standing electromagnetic fields. Each mode is typically characterized by angle, frequency, polarization, electric field strength, and/or magnetic field strength. For example, when a pulse of light is transmitted through an optical fiber, the energy can follow a number of paths that cross the fiber's longitudinal axis at different angles. A group of paths that cross the axis at the same angle is known as a mode.

multimode—supporting the propagation of more than one mode. A multimode optical fiber may be either a graded-index (GI) fiber or a step-index (SI) fiber.

optical—relating to light.

optical fiber—a filament of transparent dielectric material, usually glass or plastic, and usually circular in cross section, that guides light. An optical fiber usually has a cylindrical core surrounded by, and in intimate contact with, a cladding of similar geometry. So that the light can be guided by the fiber, the refractive index of the core is slightly different than that of the cladding.

optical signal—information carried, contained, and/or encoded in light.

perturbation—a change in a physical system.

photodetector—a transducer capable of accepting an optical signal and producing an electrical signal containing the same information as in the optical signal. As used herein a photodetector can comprise a photodiode, avalanche photodiode, PIN photodiode, photocell, photoelectric cell, photoconductor, CCD, and/or a CMOS device, etc.

photodetector array—a collection of photodetectors, typically arranged in a gridlike pattern.

pixelated photodetector—an array of transducers each capable of accepting an optical signal and, in response, producing an electrical signal indicative of information contained in the optical signal. Thus, each transducer can convert photons to electrons. Each transducer can store a picture element, or "pixel" of an overall image incident on the photodetector. As used herein a pixelated photodetector can comprise an array of photodiodes, avalanche photodiodes, PIN photodiodes, photogates, photocells, photoelectric cells, photoconductors, CCD's, CMOS image sensors, and/or active pixel sensors, etc.

plurality—more than one.

signal—detectable transmitted energy that can be used to carry information. Operationally, a type of message, the text of which consists of one or more letters, words, characters, symbols, signal flags, visual displays, or special sounds, with prearranged meaning and which is conveyed or transmitted by visual, acoustical, or electrical means. The information in a signal can be, for example digitally encrypted via for example, public key, PGP, and/or triple-DES, etc. As another example, the signal can be broadcast via, for example, a spread-spectrum technology such as, for example a frequency hopping or a direct-sequence spread-spectrum system.

signal processing module (signal processor)—a device for processing a signal. Signal processing activities can include formatting, source encoding, encrypting, channel encoding, multiplexing, modulating, frequency spreading, transmitting, receiving, frequency despreading, demodulating, sampling, detecting, demultiplexing, channel decoding, decrypting, source decoding, synchronization, analyzing, comparing, converting, transforming, Fourier transforming, interpreting, monitoring, and/or notifying, etc.

spatial—relating to an area or volume.

spatial filter—a device or method for ignoring, exposing, or detecting a spatial portion of an image and/or signal.

spatially distributed—arranged in a pre-determined pattern in a volume.

transducer—a device that converts one form of energy into another. For example, a sensing optical fiber can convert changes in mechanical energy, such as a perturbation of the fiber, to changes in optical energy.

variable—a parameter.

vital sign—a physiological sign of life and usually an indicator of a person's general physical condition. Vital signs can include movement, blood temperature, blood pressure, body temperature, pulse rate, and/or respiratory rate, etc.

wireless—any data communication technique that utilizes electromagnetic waves emitted by an antenna to communicate data (i.e., via an unguided medium), including such data communication techniques as sonar, radio, cellular, cellular radio, digital cellular radio, ELF, LF, MF, HF, VHF, UHF, SHF, EHF, radar, microwave, satellite microwave, laser, infrared, etc., and specifically excluding human voice radio transmissions, the data communication technique having a carrier frequency ranging from about 1 Hz to about $2 \times 10^{14}$ Hz (about 200 teraHertz), including all values therebetween, such as for example, about 40 Hz, 6.010 kHz, 8.7 MHz, 800 MHz, 2.4 GHz, 4.518 GHz, 30 GHz, etc. and including all subranges therebetween, such as for example, from about 100 kHz to about 100 MHz, about 30 MHz to about 1 GHz, about 3 kHz to about 300 GHz, etc. Wireless communications can include analog and/or digital data, signals, and/or transmissions.

PUBLICATIONS

The following U.S. patents are hereby incorporated by reference herein in their entirety:

20030095263 (Varshneya) "Fiber optic interferometric vital sign monitor for use in magnetic resonance imaging, confined care facilities and in-hospital";

U.S. Pat. No. 6,498,652 (Varshneya) "Fiber optic monitor using interferometry for detecting vital signs of a patient";

U.S. Pat. No. 5,291,013 (Nafarrate) "Fiber optical monitor for detecting normal breathing and heartbeat motion based on changes in speckle patterns";

U.S. Pat. No. 5,212,379 (Nafarrate) "Fiber optical monitor for detecting motion based on changes in speckle patterns";

U.S. Pat. No. 5,134,281 (Bryenton) "Microbend optic sensor with fiber being sewn thereto in a sinuously looped disposition";

U.S. Pat. No. 5,436,444 (Rawson) "Multimode optical fiber motion monitor with audible output";

U.S. Pat. No. 4,863,270 (Spillman) "Multi-mode optical fiber sensor and method";

U.S. Pat. No. 4,843,233 (Jeunhomme) "Device for detecting vibrations including a multimode optical fiber as sensitive element"; and U.S. Pat. No. 4,297,684 (Butter) "Fiber optic intruder alarm system".

DETAILED DESCRIPTION

Certain exemplary embodiments provide a patient bed with integrated sensing, which can be useful for patient monitoring. The integrated monitoring bed can automatically monitor patient movement, respiration rate, and/or pulse rate, etc.

Certain exemplary embodiments can combine an interferomatic integrating fiber optic sensor, matched spatial filtering to potentially optimize signal to noise ratio, a low cost laser pointer, a low cost digital camera, a computer such as a portable laptop PC (or other information device), and/or software, etc. Monitoring patient movement can help determine whether externally induced changes of position might be useful to prevent the occurrence of bedsores.

Certain exemplary embodiments provide a means, integrated into a patient bed, to monitor patient respiration rate, heart rate, and/or amount of movement in a continuous and nonintrusive manner. Certain exemplary embodiments provide a monitoring carpet and/or pad that can be utilized to monitor the physical activity of elderly patients and/or to alert caregivers when potentially injurious events, such as falls, occur.

Certain exemplary embodiments can facilitate the automation of health care resulting in the potential reduction of certain medical errors. Certain exemplary embodiments can monitor movement of bed-ridden patients thereby limiting the possibility of bedsores developing. Certain exemplary embodiments can monitor movement of an individual on a carpet or pad. If an individual does not move for a predetermined period of time, certain exemplary embodiments permit automated notification of that fact.

A patient's vital signs can be monitored using periodic and/or intrusive monitoring wherein a health care practitioner manually monitors patients vital signs using separate monitoring equipment. With the ever-increasing average age of the population and decreasing number of nursing and other health care support personnel, it can be desirable to automate biomedical measurements thereby freeing up medical staff to concentrate on critical care. Certain automations can be achieved via use of optical fiber sensing technology.

When a pulse of light is transmitted through an optical fiber, the energy can follow a number of paths that cross the fiber's longitudinal axis at different angles. A group of paths that cross the axis at the same angle is known as a mode. The lowest order mode, which is also known as the fundamental mode and the $LP_{01}$ mode, is the mode in which light passes substantially parallel to the fiber axis. In modes other than the fundamental mode, known as high order modes, the light bounces from one side to the other all the way down the fiber. Fibers that have been designed to support only one mode with minimal loss, the fundamental mode, are known as single mode fibers. A multi-mode fiber is a fiber whose design supports multiple modes, and typically supports over 100 modes.

In certain exemplary embodiments, a monochromatic light source, such as a laser diode, can input coherent light into a multi-mode optical fiber segment that is subject to environmental perturbations. The coherent light, as it travels through the core, can assume different modes, including a lowest order mode and at least one higher order mode. The various modes can constructively and destructively interfere to produce a characteristic speckle pattern that can be projected through a spatial filter onto a photo-detector. In its simplest form, the spatial filter can be defined by a light-blocking and/or light-absorbing sheet having one or more apertures, such as circular holes, that pass a subset of the speckle pattern to the photodetector. The signal output of the photodetector can vary in response to the variation in the intensity distribution of that portion of the speckle pattern passed to the photodetector by the spatial filter. The output of the photodetector can be provided to a signal processor with the change in the intensity distribution functionally related to the sensed perturbations.

Certain sensing techniques for detecting changes in inter-mode interference patterns in response to external environmental perturbations are described in Spillman et al., "Statistical Mode Sensor for Fiber Optic Vibration Sensing Applications", Applied Optics 28, No. 15, 3166–3176, 1989. Such sensing techniques are not believed to have been previously used in an integrated monitoring system for monitoring patients' vital signs.

Certain exemplary embodiments relate to an integrated monitoring bed for monitoring patient vital signs and/or activity level, and/or to an integrated monitoring carpet/pad for monitoring patient vital signs and/or activity level.

In certain exemplary embodiments, the bed can utilize a sensing technique comprising a multimode fiber optic sensor. Optical energy transmitted through the core of an optical fiber, either a single or multi-mode core, can be affected by physical perturbations of the fiber. The physical perturbation can alter the index of refraction of the core material and/or the differential indices between the cladding and the core in such a way that the optical energy transmitted through the core can be changed. The physical perturbation can be caused by tension- or compression-induced strain and/or strain induced by bending the fiber about a small radius (i.e., micro-bending) or large radius bending (i.e., macro-bending). Accordingly, an optical fiber can be used as a sensor to measure a physical parameter by correlating changes in the output energy with the environmental perturbations.

The energy output from the sensing fiber can be analyzed, for example, in terms of quantitative changes in intensity, wavelength, and/or polarization states. In a more sophisticated context, the output light can be interferometrically compared against a reference source to provide an interferometer pattern that can be empirically correlated with the fiber-perturbing parameter. In the interferometric context, e.g., a Mach-Zender interferometer, coherent source light can be passed through reference and sensing fibers with the light from the two paths combined to form an interferometric pattern that can be analyzed to provide information that is functionally related to an external perturbation affecting the sensing fiber path.

Certain exemplary embodiments can provide a multi-mode optical fiber sensor and/or method for measuring physical perturbations using interferometric parameter analysis of perturbation-affected light propagated through a multi-mode optical fiber. Certain exemplary embodiments can provide a multi-mode optical fiber sensor and/or method that reduces the optical fiber requirements in an application by providing a multi-function multi-mode optical fiber in which the measurement of physical perturbations using interferometric parameter analysis can be performed in conjunction with other functions, including data transmission, communications, control, and/or telemetry. Certain exemplary embodiments can provide a multi-mode optical fiber sensor and method in which coherent monochromatic radiation from a optical energy source passes through a multi-mode optical fiber that is subjected to an external perturbation. As the light is conducted through the core, the various modes can constructively and destructively interfere with one another with the projected output having a characteristic inter-modal "speckle" pattern. A detector, such as a two-dimensional staring array, can output an electrical signal in response to the intensity distribution of the speckle pattern. As the fiber or a segment thereof is perturbed, the inter-modal interference pattern and/or the intensity distribution can change in a manner functionally related to the perturbation. The corresponding output of the detector can be analyzed by a signal processor to provide a signal output representative of the perturbation.

In certain exemplary embodiments, the output light from the multi-mode optical fiber can be projected onto a multi-pixel CCD array. As the CCD array is scanned, its outputs can be sent to a signal processor that converts the individual pixel output into a corresponding digital value and/or stores the digitized array output as two successive data frames. The absolute value of the change between corresponding pixel data points in the two data frames can be summed to provide a signal output that is functionally related to the sensed perturbations.

In certain exemplary embodiments, a fiber perturbation region or zone can be defined in which the multi-mode fiber optic sensor is sensitive to perturbation only within the defined region, for example, by providing single mode input and output optical fiber with a intermediate multi-mode optical fiber that is subjected to and senses the perturbations. The light can be output through a spatial filter and/or one or more lenses, such as a ¼ pitch gradient index rod lens, to another multi-mode optical fiber segment that can carry the light to the photodetector for processing.

Certain exemplary embodiments can provide a multimode optical fiber sensor in which the constructive and destructive interference of coherent light in a multi-mode fiber provides optical information useful in providing a signal that is functionally related to the sensed perturbation. Additionally, the sensing optical fiber can be used to also transmit other data, such as communications, control, telemetry, etc., on wavelength bands outside that used to provide perturbation sensing to provide a multi-function optical fiber.

FIG. 1 is a block diagram of an exemplary embodiment of a multimode fiber optic sensor 1000. Light from a coherent light source 1100 can be coupled to a multimode optical fiber 1200. Light exiting fiber 1200 can form a complex speckle pattern due to intermodal interference. If fiber 1200 is perturbed, such as by a perturbation F, fiber 1200 can experience mechanical flexing and/or bending, which can cause the distribution of power in the pattern to change but not the total power. In other words, some speckles decrease in power while others increase in power during perturbation, but the total power is unaffected. Light can be output from fiber 1200 and its speckle pattern can be sensed by to a photodetector 1300, such as a photodetector array, a charge coupled device (CCD), complementary metal oxide semiconductor (CMOS) device, and/or a spatial detector array. Photodetector 1300 can generate a signal 1400, which can be processed by a signal processor 1500. The signal processor can sample the whole speckle pattern and/or any portion thereof, and/or can store any portion of the pre-sampled or sampled pattern in a memory device. The pattern can be sampled again and the sum of the absolute values of the intensity changes seen by the pixels of the array can be computed and/or output. The process can then be repeated.

If the integrated perturbation is symbolized as P, and time is symbolized as t, then it has been shown that fiber output is proportional to the absolute value of dP/dt or ΔP/Δt, such that for any sensor output at frequency w, the perturbation causing that output would be at w/2. Such a fiber is sometimes referred to as a Statistical Mode (STM) sensor.

It has also been shown in Spillman and Huston, "Scaling and Antenna Gain in Integrating Fiber Optic Sensors", Journal of Lightwave Technology 13, No. 7, 1222–1230, (1995), and in Huston et al., "Monitoring Microfloor Vibrations with Distributed Fiber Optic Sensors", Proc. SPIE 3671, 118–125, 1999, that the signal to noise ratio of an integrating sensor can be significantly improved by matching the spatial pattern of the integrating sensor to the parameter field of interest (e.g., via matched filtering and/or preprocessing). It has been discovered that the spatial distribution of the sensor can be matched to the distribution of displacement produced by, for example, respiration and/or heartbeat, thereby improving the signal to noise ratio of the sensor.

Figure 2:
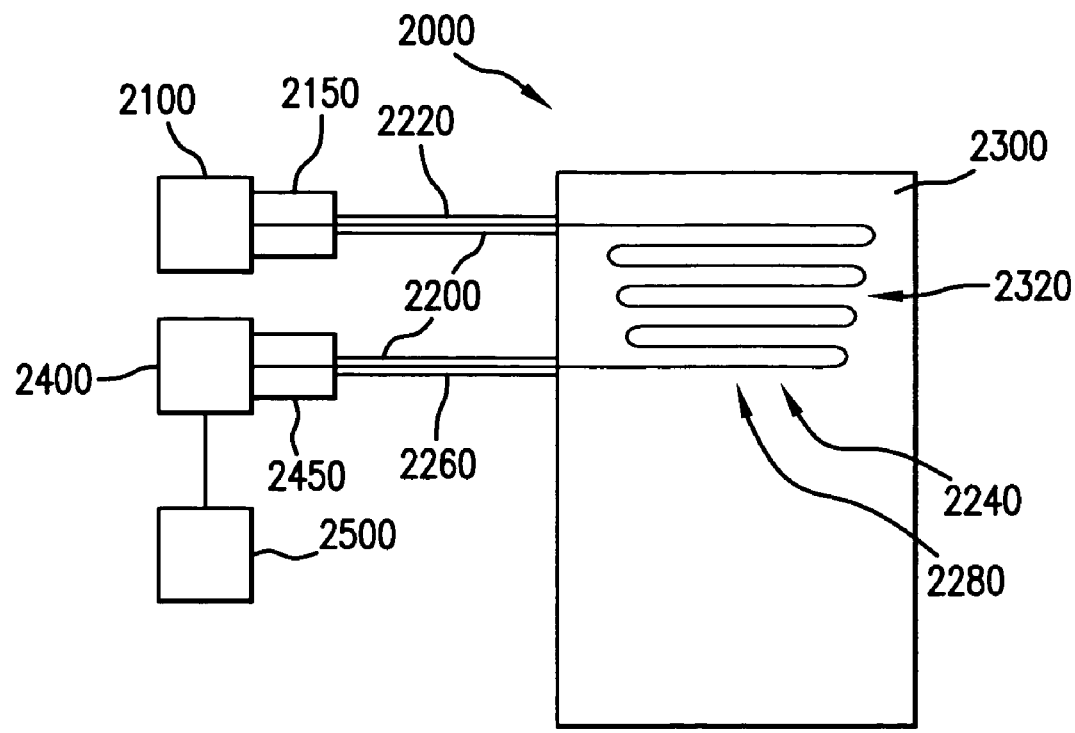
FIG. 2 is a block diagram of an exemplary embodiment of an integrated monitoring device.

FIG. 2 is a block diagram of an exemplary embodiment of an integrated monitoring device 2000 that can comprise an STM sensor. Light from a coherent optical source 2100, such as a laser pointer, can be coupled into a multimode optical fiber 2200, which can be held stationary by a first mechanical fiber/source coupling element 2150. That portion of fiber 2200 positioned between coupling element 2150 and a target region 2320 of the bed 2300 can be contained within a first mechanical damping element 2220. The sensing region 2240 of fiber 2200 can be spatially distributed and/or configured in a pattern 2280 chosen to optimize response to respiration, heart rate, and/or movement. For example, for respiration, target region 2320 might be generally defined between an expected position on bed 2300 of the shoulders of a patient and an expected position on bed 2300 of the hips of the patient. Thus, sensing region 2240 and/or pattern 2280 can be generally placed within, on, and/or adjacent, target region 2320. Pattern 2280 of sensing region 2240 can be serpentine, spiral, irregularly meandering, etc., and can include as many curves and/or turns as needed, and/or can be distributed over as large a percentage of target region 2320 as needed, to optimize response to a targeted vital sign and/or other perturbation. Because the spatial distribution of pattern 2280 and/or sensing region 2240 can be matched to a targeted perturbation, pattern 2280 and/or sensing region 2240 of fiber 2200 can be considered to be a spatial filter.

Fiber 2200 can enter a second mechanical damping element 2260 and can extend to a second mechanical coupling element 2450 that can hold an end of fiber 2200 in the appropriate stationary position to optimally excite a two dimensional photodetector array 2400, such as a digital camera. Individual pixel intensities then can be transmitted from photodetector 2400 to a computer 2500, such as a laptop personal computer, for processing as indicated herein.

Fiber 2200, which can serve as a filter fiber-sensing element, can alternatively be disposed in a carpet or pad (not shown). Pattern 2280 and/or sensing region 2240 of fiber 2200 can be determined by the needs of the application. The upper region (above the legs of a patient) of a monitoring bed can be the only target region 2320 covered by sensing region 2240, or sensing region 2240 can cover the entire patient resting region of a monitoring bed 2300. In certain exemplary embodiments, one or more additional integrating fiber optic sensors can be added to the integrated monitoring bed, if desired for additional sensitivity and/or to target other types of perturbations. Alternatively, the entire area of a carpet or pad can correspond to target region 2320 according to the desired application.

Figure 3:
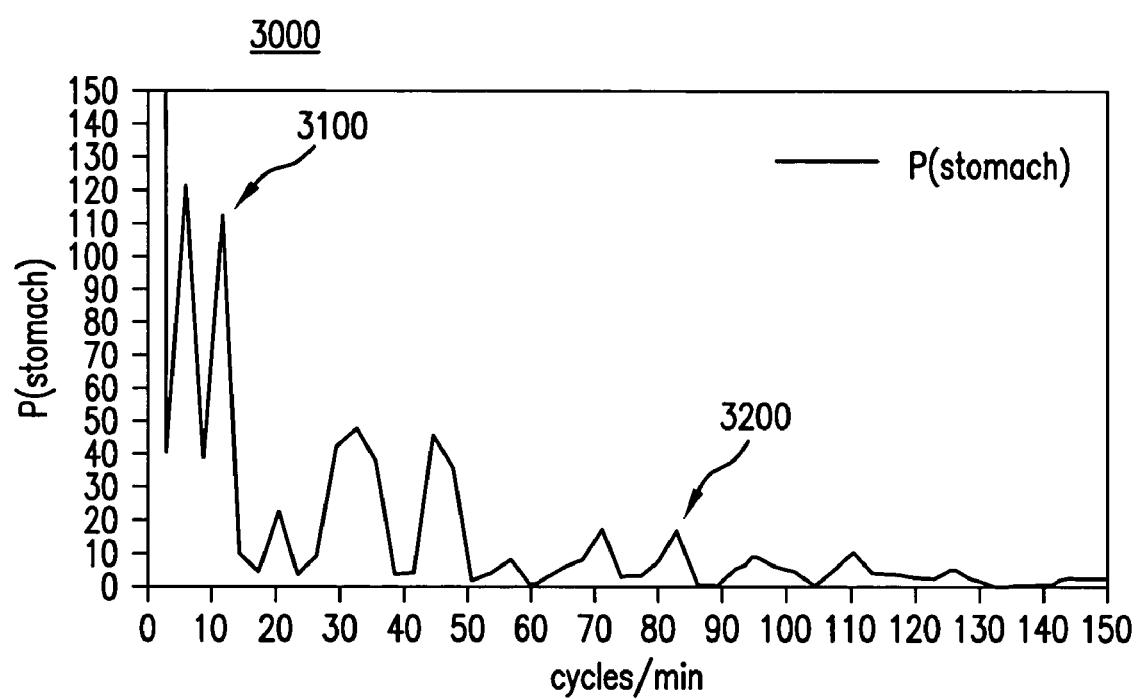
FIG. 3 is a Fourier transform of data generated by a test subject lying on her stomach in an exemplary embodiment of an integrated monitoring bed depicted in FIG. 2.

A number of experimental runs have been made with test subjects in the four most typical sleep positions, i.e., on back, stomach, and left and right fetal positions. FIG. 3 is a plot 3000 of discrete Fourier transformed data generated by a test subject lying on her stomach in an exemplary embodiment of an integrated monitoring bed depicted in FIG. 2 and utilizing an STM sensor. The frequency axis has been corrected for the fact that the sensor output produces signals at twice the frequency of the perturbation. Although the system was not optimized when the measurements were made as, with respect to FIG. 3, the sampling rate was too high, signals corresponding to both the respiratory rate 3100 and the heart rate 3200 can be seen clearly.

In certain exemplary embodiments, any generic long gauge length sensor, fiber optic or otherwise, can be used as a perturbation sensor. In terms of fiber optic technology, some of the sensors that can be used can be based on intermodal interference, mode angle shifting, single mode polarmetric shifts, single mode interferometers (Mach-Zheirder, Michaelson), microbending, arrays (serial) of Fabrey-Perot cavities, and/or arrays (serial) of Bragg gratings, etc.

Figure 4:
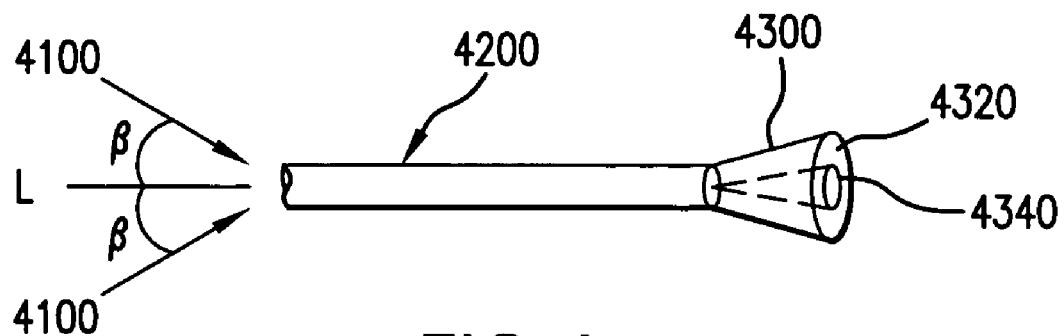
FIG. 4 is a side view of an exemplary embodiment of a multimode optic fiber.

Certain exemplary embodiments can utilize a sensor based on mode angle shifting, or a High Order Mode Excitation (HOME) sensor, which can output a signal that is proportional to a fiber perturbation. FIG. 4 is a side view of an exemplary embodiment of a fiber portion 4000 of such a sensor, which can comprise a multimode optic fiber 4200, into which light 4100 is injected at a non-zero incidence angle β, as measured from the longitudinal axis L of the fiber. That is, rather than being introduced exactly parallel to longitudinal axis L, the light has a radial component as well.

This means that the light output 4300 from fiber 4200 will be in the shape of a cone, having a lighted portion 4320 and an unlighted portion 4340. When fiber 4200 is perturbed however, the modes of the light can change, potentially shifting into higher order modes and/or lower order modes. Either type of shift can cause the dimensions and/or shape of lighted portion 4320 and/or unlighted portion 4340 to change. Changes in dimensions and/or shape of lighted portion 4320 and/or unlighted portion 4340 can be detected by a photodetector, such as a pixelated detector (e.g., digital camera, CCD detector, CMOS detector, etc.) and/or a non-pixelated detector (e.g., a large area photodetector). Thus, a photodetector can be positioned, for example, within a circular area normally surrounded and bordered by an annulus created by higher order modes. The photodetector can detect perturbations that result in the excitation of, coupling of, and/or shifting to, lower order modes the light of which is incident within the circular area.

Figure 5:
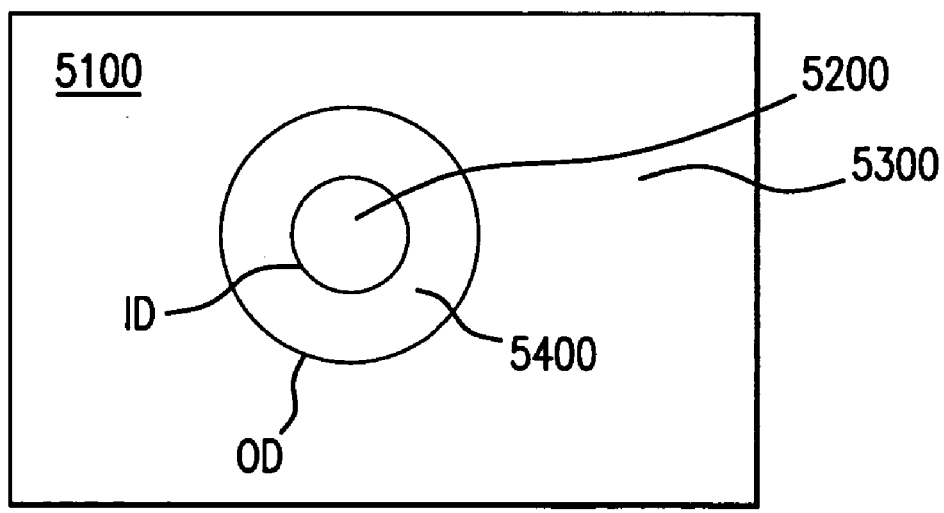
FIG. 5 is a front view of a projection on a flat screen of an output from the exemplary embodiment of FIG. 4.

FIG. 5 is a front view of an exemplary projection 5000 on a flat screen 5100 of an output 4300 from the exemplary embodiment of FIG. 4. Projection 5000 can comprise an inner unlighted portion 5200, an outer unlighted portion 5300, and a lighted portion 5400. If the fiber is circular in longitudinal cross-section and flat screen 5100 is oriented perpendicular to the longitudinal axis of the fiber, then unlighted portion 5200 can be circular and/or lighted portion 5400 can be annular.

When the fiber pattern on the monitoring bed is perturbed by motion due to respiration or heartbeat, the inner radius and/or outer radius of the annulus changes, so that if a spatial filter is used that only intercepts a portion of the annular pattern of light and allows it to pass to a detector, an output signal will result containing information about the perturbation. For example, assuming that the outer radius of the annulus increases due to a perturbation, if a spatial filter only passes light that intercepts at least a portion of the area defined only by the increased outer radius, then the fact of the perturbation can be sensed. That is, the spatial filter can pass light that falls within a sector defined between the pre-perturbation outer circumference and the perturbation-caused outer circumference. Likewise if the perturbation decreases a radius, diameter, and/or circumference of the annulus, the spatial filter and/or signal processor can detect the resulting change in the projected light pattern and/or intensity.

Figure 6:
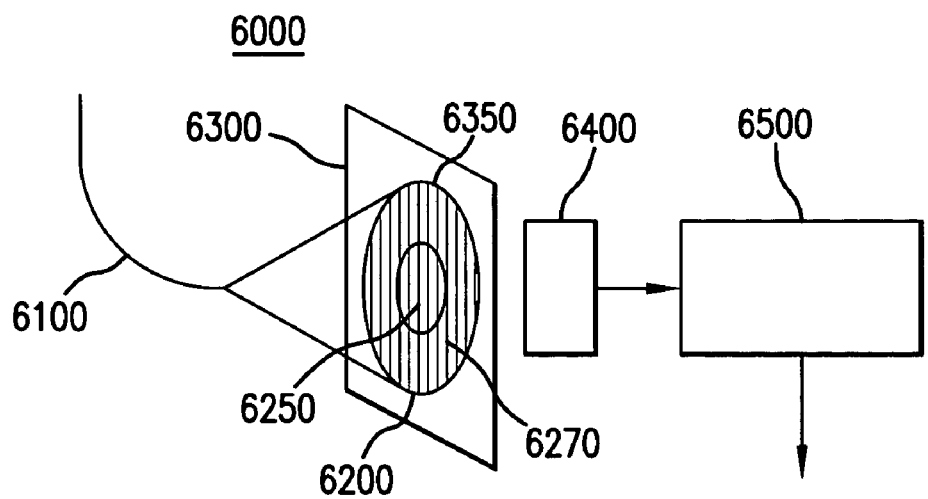
FIG. 6 is a block diagram of an exemplary embodiment of a system 6000.

FIG. 6 is a block diagram of an exemplary embodiment of a system 6000 that comprises a HOME sensor. In FIG. 6, an optical fiber 6100 can output a light pattern 6200, such as a speckle pattern, which can be projected onto and through a spatial filter 6300 onto a photodetector 6400. The spatial filter 6300, in a simple physical form, can be fabricated from a opaque sheet having one or more apertures so that a portion of the speckle pattern, indicated generally at 6250, is blocked and a portion or subset 6270 thereof is allowed to pass to the photodetector 6400. Assuming a constant light input to fiber 6100, the intensity of the total circular speckle pattern 6200 remains substantially constant over time, even when fiber 6100 is perturbed, because the average increase in intensity of some of the speckles will be statistically averaged with the average decrease in intensity of other of the speckles. Accordingly, the spatial filter 6300 can function to expose only a portion or subset of the speckle pattern 6200 to the photodetector 6400, so that a change in intensity can be detected. In general, the subset of the speckle pattern 6200 provided by the spatial filter 6300 to the photodetector 6400 can be sufficiently large so that an adequate signal-to-noise ratio is obtained and sufficiently small so that statistical averaging effects do not prevent discrimination of the perturbation effect in the speckle pattern 6200. The shape of the aperture of the spatial filter 6300 is shown in FIG. 6 as an annular opening 6350, although the shape of the aperture or apertures in the spatial filter 6300 may be varied, such as for example, to form a predetermined rectangular matrix of circular holes. The photodetector 6400 can output an electrical signal in response to the intensity of the subset 6270 of speckle pattern 6200 imaged onto the photodetector 6400 through the spatial filter 6300 so that variations in the intensity will provide a corresponding output.

A signal processor 6500 can accept the output of the photodetector 6400 and processes the signal to obtain an information signal functionally related to the perturbation. Since any movement of optical fiber segment 6100 can cause a change in the intensity of the speckle pattern 6200 imaged onto the photodetector 6400, the movement of optical fiber segment 6100 can cause a corresponding change in the signal output of the photodetector 6400. The processing provided by signal processor 6500 can include any of formatting, source encoding, encrypting, channel encoding, multiplexing, modulating, frequency spreading, transmitting, receiving, frequency despreading, demodulating, sampling, detecting, demultiplexing, channel decoding, decrypting, source decoding, synchronization, analyzing, comparing, converting, transforming, Fourier transforming, interpreting, monitoring, and/or notifying, etc.

Figure 7:
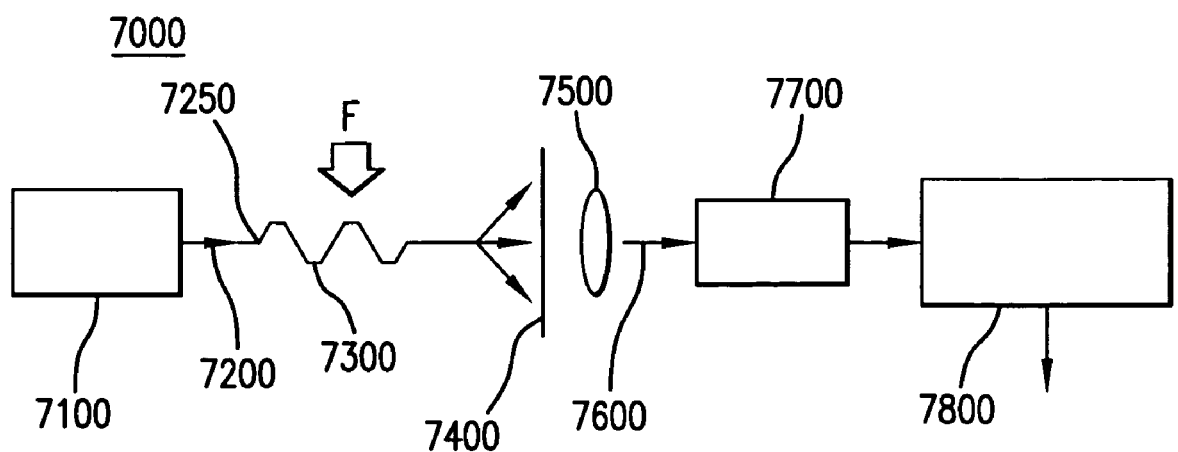
FIG. 7 is a block diagram of an exemplary embodiment of a system 7000.

FIG. 7 is a block diagram of an exemplary embodiment of an STM and/or HOME system 7000. As shown, an optical source 7100 can couple coherent radiation into a single-mode optical fiber segment 7200 that is coupled at 7250 to a multi-mode optical fiber 7300 that is subjected to the perturbations F to be sensed, thereby reducing error from undesired vibrations. After the desired perturbation F has been sensed by the multi-mode optical fiber segment 7300, the complex interference pattern is output from the multi-mode optical fiber segment 7300 through a spatial filter 7400. A subset of the complex interference patter passes through the spatial filter 7400 and is focused through a lens 7500 into a multi-mode optical fiber segment 7600. The complex interference pattern is transmitted along the multi-mode optical fiber segment 7600 to a photodetector 7700, which outputs a signal in response to the intensity of the subset of the complex interference pattern passed by the spatial filter 7400. The signal is output to a signal processor 7800 for analysis in a manner analogous to that described above for the embodiment of FIG. 6.

Figure 8:
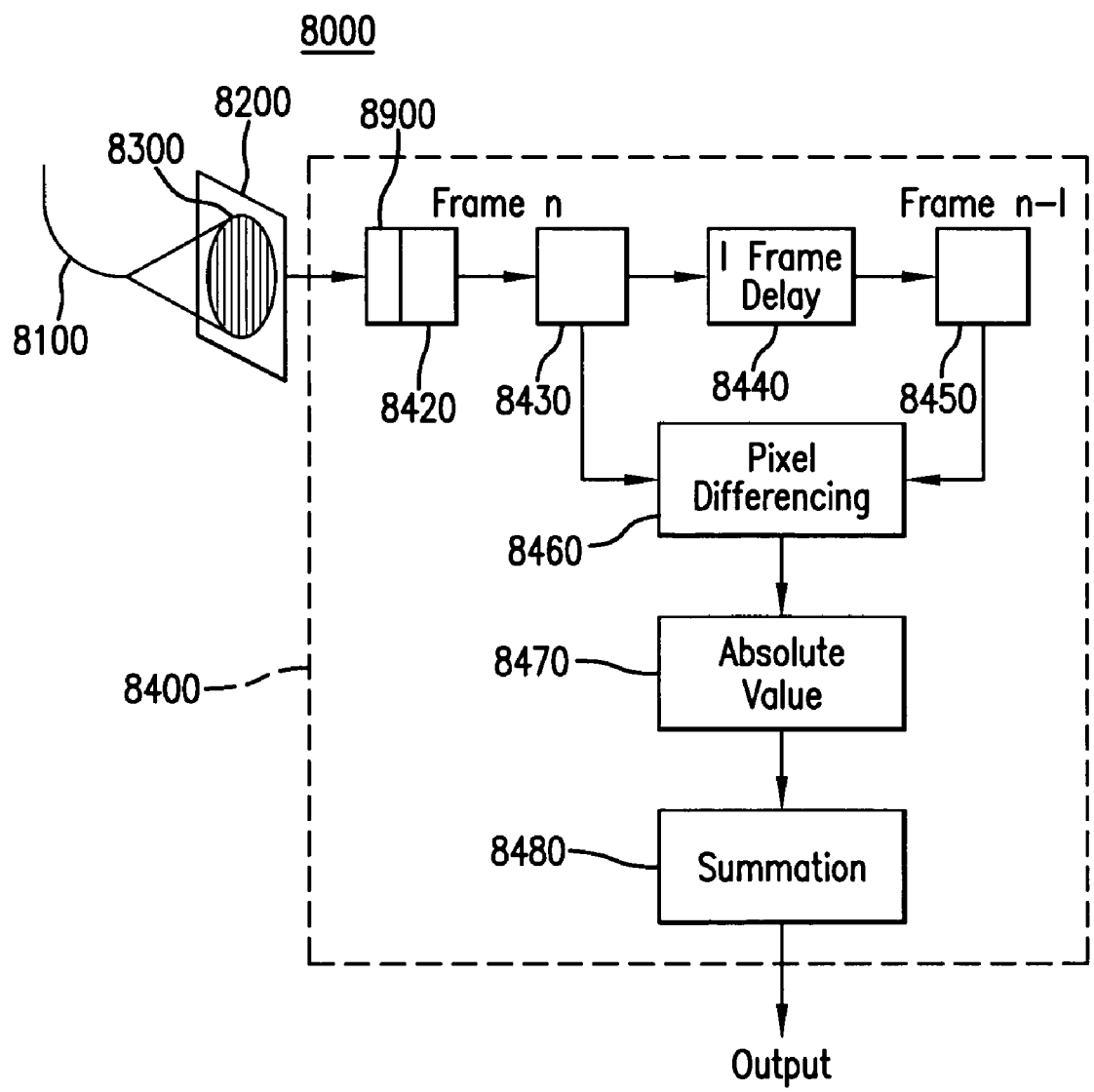
FIG. 8 is a block diagram of an exemplary embodiment of a system 8000.

FIG. 8 is a block diagram of an exemplary embodiment of a system 8000. As shown therein, coherent, monochromatic radiation can be provided to a multi-mode optical fiber segment 8100. The complex interference pattern produced by the optical fiber segment 8100 can be output onto a CCD array 8200 as a characteristic speckle pattern 8300. The CCD array 8200 can be located a sufficient distance from the output end of the optical fiber segment 8100 so that a pixel on the CCD array 8200 is smaller than an average speckle feature; each pixel thereafter can generate a signal in response to the intensity of radiation incident on that pixel.

A signal processor 8400 can accepts the output of the CCD array 8200 and can analyze the information in a frame-by-frame manner with between a first frame and its immediately preceding frame providing information that is functionally related to the perturbation. More specifically, the intensity of the energy sensed by each pixel of the CCD array 8200 can be digitized by a digitizer 8420 and/or stored in a first frame buffer 8430. This initial frame data can be transferred to a frame delay buffer 8440, which can hold the frame data for a selected time period, as another data frame is stored in the first data frame buffer 8430. The initial frame data in the frame delay buffer 8440 then can be transferred to the second data frame buffer 8450. Accordingly, a preceding $(n-1)^{th}$ data frame can be held in the data frame buffer 8450 and a subsequent $n^{th}$ data frame can be held in the data frame buffer 8430. Each buffer can take the form of a conventional memory with multi-bit memory locations that correspond to pixels in the CCD array 8200. A differencing circuit 8460 then can compare the contents of the data frame buffers 8430 and 8450 on a pixel-by-pixel basis and can convert the intensity differences into corresponding absolute values by an absolute value circuit 8470, which circuit can include memory locations that correspond to pixels of the CCD array 8200. Lastly, the changes in intensities of the pixels of the CCD array 8200 can be accumulated in a summing circuit 8480 to obtain a final value, which can be output to a memory, a recording device, and/or a display. As successive data frame differences are determined, the final value output will vary as the sensing fiber segment 8100 is perturbed. Thus, the signal processor 8400 can precisely measure the perturbation of the optical fiber segment 8100 by measuring the change in intensity of each individual speckle of the speckle pattern 8300 on the CCD array 8200.

As in the case of the embodiment of FIG. 8, a subset or portion of the speckle pattern 8300 can be evaluated to provide information functionally related to the perturbation. Although an physical spatial filter can be employed in a manner analogous to that of FIG. 7, the same functional result can be obtained in the embodiment of FIG. 8 via a virtual spatial filter 8410 of signal processor 8400 that disregards or does not pass the output of a selected percentage and/or selected spatial portion of the pixels of the CCD array 8200 so that statistical averaging will not affect the ability to discriminate perturbations in the speckle pattern 8300.

Figure 9:
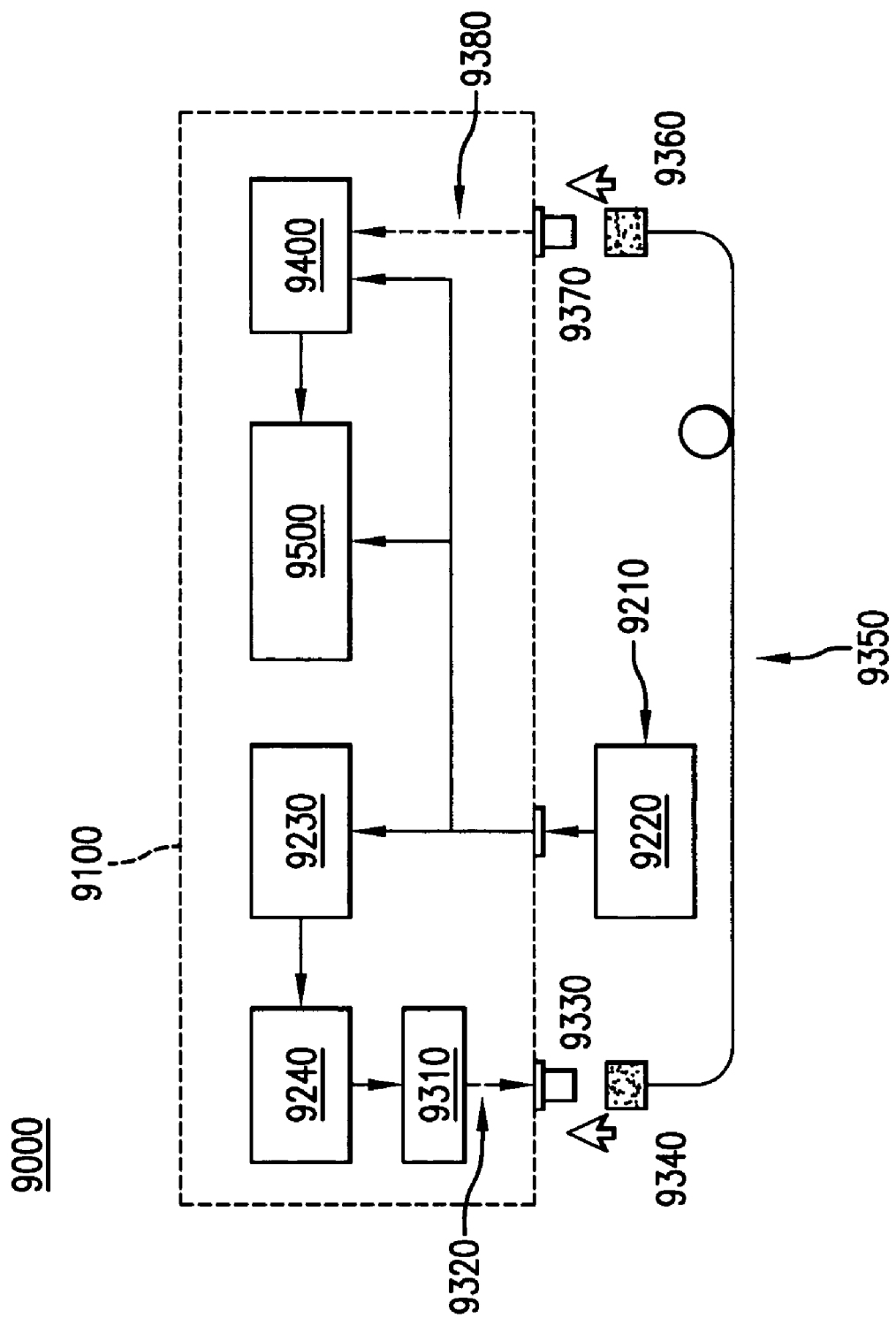
FIG. 9 is a block diagram of an exemplary embodiment of a system 9000.

FIG. 9 is a block diagram of an exemplary embodiment of a wireless optical fiber sensing system 9000, which can include two portions: a remote portion that can comprise a light source, sensing fiber, CCD camera and wireless transmitter; and a local portion (not shown) composed of wireless receiver and processing laptop.

The remote portion can include a remote wireless module 9100. External to module 9100, an power source 9210, such as an alternating current approximately 110–120 volt power source, can provide electrical power to an alternating current to direct current adapter 9220, which can plug in to module 9100 to provide direct current to the light source, camera 9400, and/or wireless transmitter 9500.

Within module 9100, a direct current voltage regulator 9230 can regulate voltage to about 2.5 volts, and provide current to a driver 9240 of an optical source 9310, such as a laser diode. Light 9320 can be produced and emitted by optical source 9310. The optical output of optical source 9310 can be coupled to a segment of sensing fiber 9350 via an FC mating sleeve 9330 and a bare fiber adapter 9340. Similarly, sensing fiber 9350 can be mechanically coupled to module 9100 via bare fiber adapter 9360 and FC mating sleeve 9370. Light 9380 output by fiber 9350 can be received by a CCD camera 9400. Sampled frames of the far-field speckles perceived by camera 9400 can be sent to the local portion through a wireless transmitter 9500.

Figure 10:
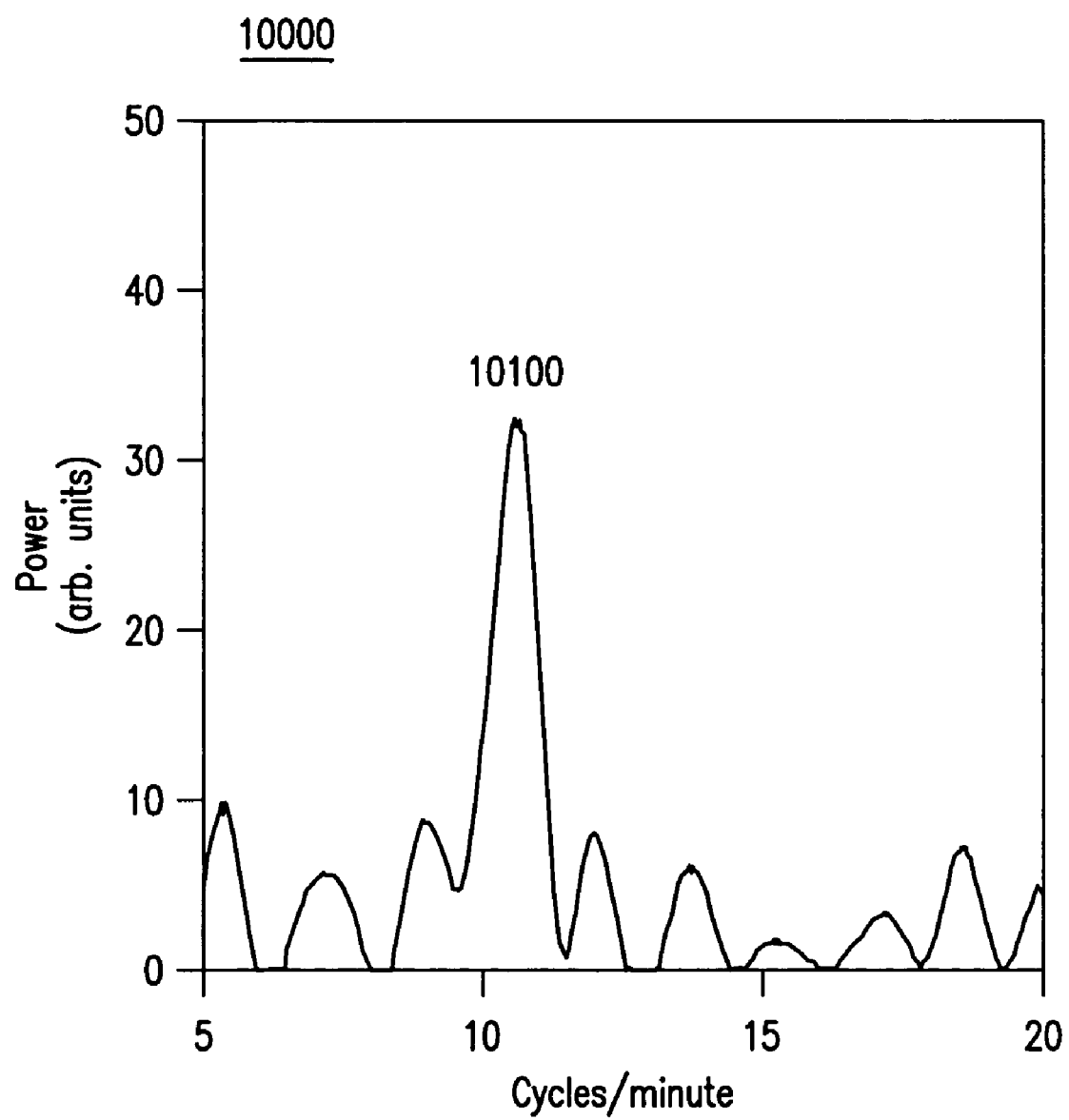
FIG. 10 is a plot of power versus frequency data generated by an exemplary embodiment of the optical fiber sensor of FIG. 6.

FIG. 10 is a plot 10000 of power versus frequency data generated by an exemplary embodiment of a HOME optical fiber sensor. The frequency data was obtained via Fourier transform. The plot shows a peak 10100 at about 11 cycles/minute, which corresponds to the respiration rate of the patient.

Figure 11:
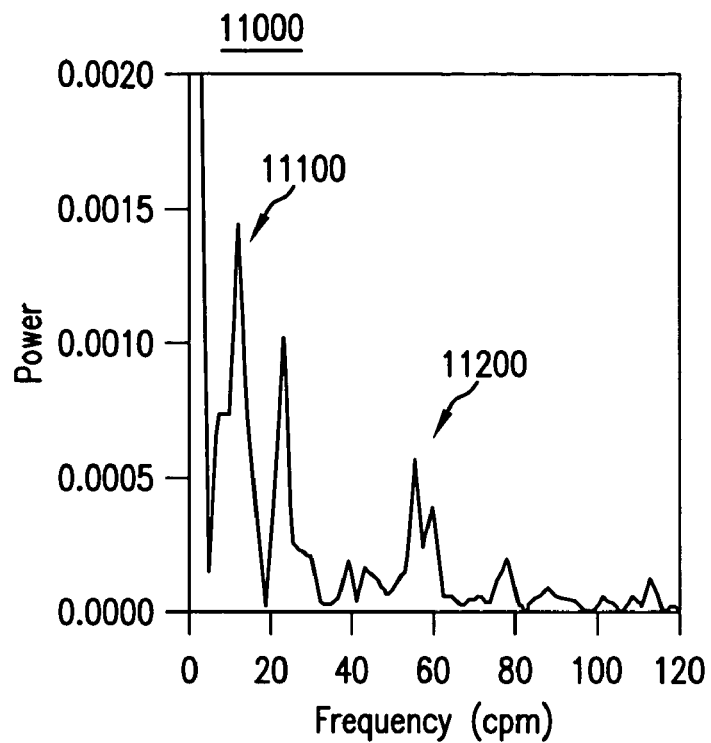
FIG. 11 is a plot of power versus frequency data generated by an exemplary embodiment of the optical fiber sensor of FIG. 6.
Figure 12:
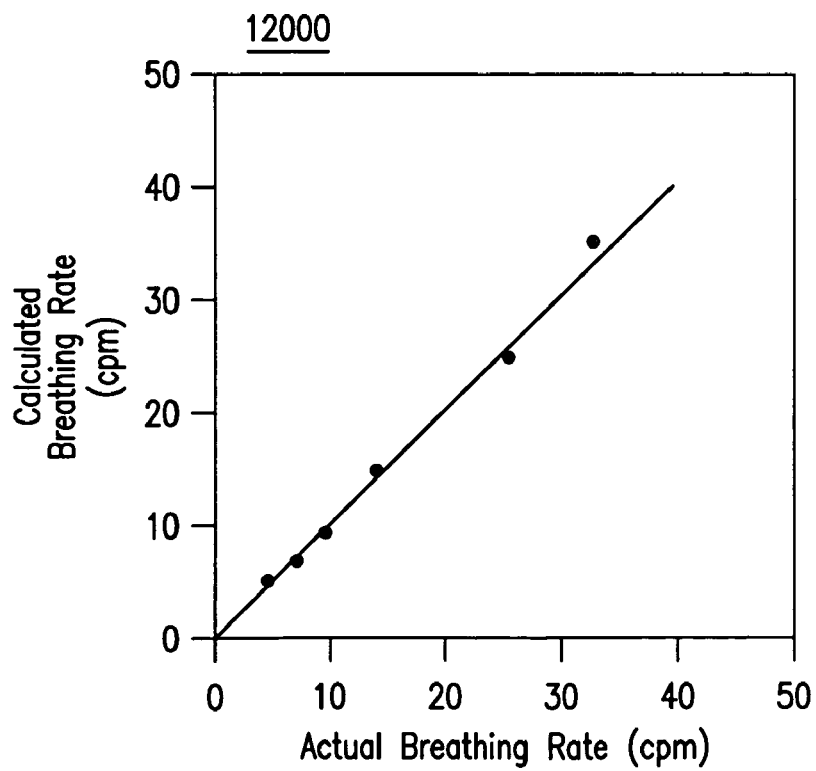
FIG. 12 is a plot correlating calculated respiration rate vs. actual breathing rate for data gathered via an exemplary embodiment of the optical fiber sensor of FIG. 6.

FIG. 11 is a plot of power versus frequency data generated by an exemplary embodiment of a HOME optical fiber sensor. The frequency data was obtained via Fourier transform. The plot shows a peak 11100 at about 10–15 cycles/minute, which corresponds to the respiration rate of the patient, and a peak at about 55–60 cycles/minute, which corresponds to the heart rate of the patient. FIG. 12 is a plot correlating calculated respiration rate vs. actual respiration rate for data plotted in FIG. 11.

Figure 13:
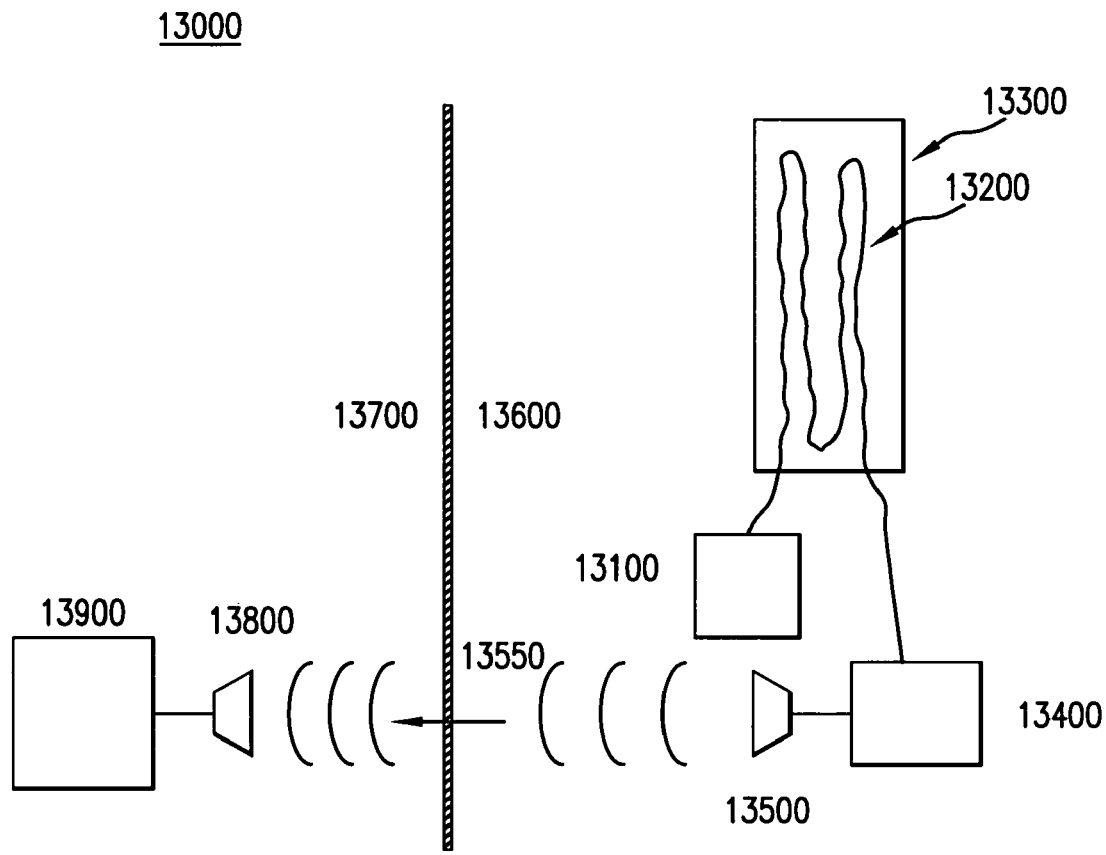
FIG. 13 is a block diagram of an exemplary embodiment of a system 13000.

FIG. 13 is a block diagram of an exemplary embodiment of a wireless optic fiber sensing system 13000. A light source 13100 can couple coherent light to an optical fiber 13200 which is distributed in a predetermined pattern on, above, and/or adjacent a human support structure 13300, such as a bed, mattress, mattress pad, chair, seat, carpet, carpet pad, and/or floor, etc. In certain exemplary embodiments, the optical fiber can be a 200 micrometer core silica multimode optical fiber arranged in two sinusoidal overlapping patterns arranged orthogonal to each other so that the fiber in each pattern crosses the fiber in the other pattern at an angle of 90 degrees. The light source can be, for example, a DIY laser pointer from Laser Magic Co. of Costa Mesa, Calif., which can provide an output of 5 mW@645 nm. Output from optical fiber 13200 can be detected by a photodetector 13400 and an electrical signal generated thereby can be provided to a wireless transmitter 13500, which can output an electro-magnetic signal 13550 from a first zone 13600, such as a patient's room, to a second zone 13700, such as a nurse's station. The photodetector and wireless transmitter can be provided as a module, such as for example a GrandTec RFC-3000 wireless CCD module (provided by GrandTec USA of Dallas, Tex.), potentially with an accompanying wireless receiver. The electro-magnetic signal 13550, which can be transmitted at, for example, about 2.4 GHz, can be received by a wireless receiver 13800 and provided, for example via a USB 2.0 interface, to an information device 13900, which can comprise a signal processor. The receiver, information device, and/or signal processor can potentially handle signals from multiple sensors and/or transmitters. The sampling rate can be, for example, about 30 frames/second. The information device can run a software program designed for processing received signal and/or data encoded therein, calculating appropriate values, such as the Sum of Pixel Differences (SPD) values of adjacent frames, and rendering (i.e., making perceptible) the SPD values in real time possibly in combination with the received frames. The software program can be written in any computer language or tool, such as Visual C++ 6.0 by Microsoft of Redmond, Wash. The software program can automatically load a default video source that is coupled to the information device. The software program can save and/or output the SPD values to a predetermined and/or user-specified drive and/or file. The saved file can be in any format, including text, Excel, etc. The software program can provide a graphical user interface.

Figure 14:
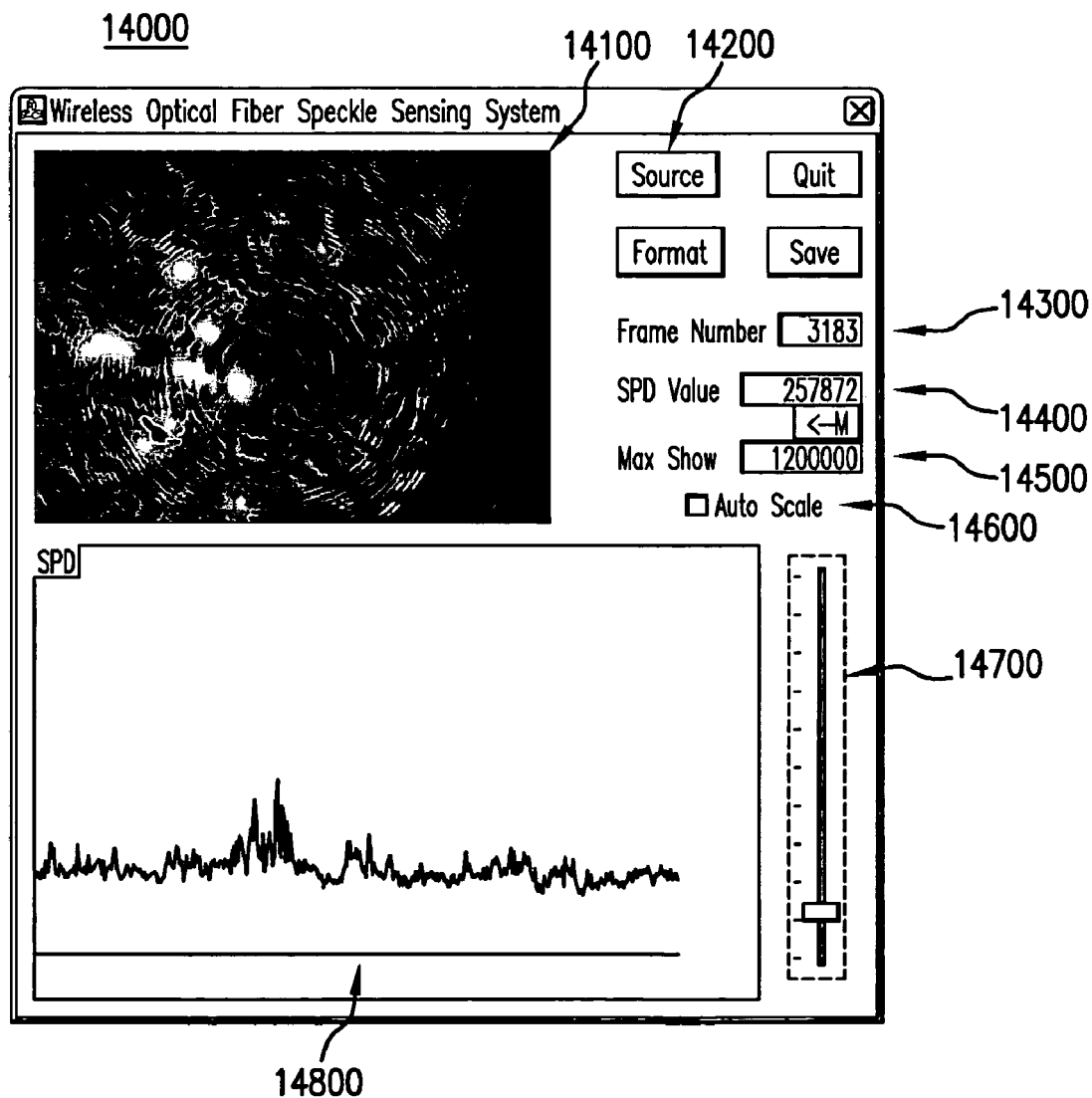
FIG. 14 is an exemplary user interface 14000 for a wireless optical fiber speckle sensing system.

FIG. 14 is an exemplary user interface 14000 for a wireless optical fiber speckle sensing system. User interface 14000 can include a wide variety of user interface elements, such as an image 14100 of the detected light incident upon the photodetector, the light received by the signal processor, and/or the light processed by the signal processor after filtering and/or preprocessing. Additional user interface elements can include a video source feature and/or parameter button 14200, a frame indicator and/or control 14300, a Sum of Pixel Difference (SPD) indicator and/or control 14400, a maximum SPD indicator and/or control 14500, an autoscale control 14600, an SPD scale indicator and/or control 14700, and/or a plot 14800 of SPD intensity versus time and/or location, etc.

FIG. 15 is an exemplary user interface 15000 for advanced video source features and/or parameters. User interface 15000 can include a wide variety of user interface elements, such as tabs 15100, 15200, 15300, 15400 for switching between various groups of video source features and/or parameters. User interface 15000 also can include a video standard indicator and/or control 15500, a maximum bandwidth indicator and/or control 15600, a consumed bandwidth indicator 15700, a horizontal offset indicator and/or control 15800, and/or a vertical offset indicator and/or control 15900, etc.

FIG. 16 is an exemplary user interface 16000 for capture source features and/or parameters. User interface 16000 can include a wide variety of user interface elements, such as video device selector 16100 and/or video source indicator and/or control 16200.

FIG. 17 is an exemplary user interface 17000 for video device settings. User interface 17000 can include a wide variety of user interface elements, such as indicators, selectors, and/or controls for brightness 17100, contrast 17200, hue 17300, saturation 17400, sharpness 17500, white balance 17600, gamma 17700, and/or backlighting 17800, etc.

FIG. 18 is an exemplary user interface 18000 for camera controls. User interface 18000 can include a wide variety of user interface elements, such as indicators, selectors, and/or controls for zoom 18100, focus 18200, exposure 18300, iris 18400, tilt 18500, pan 18600, and/or roll 18700, etc.

Figure 19:
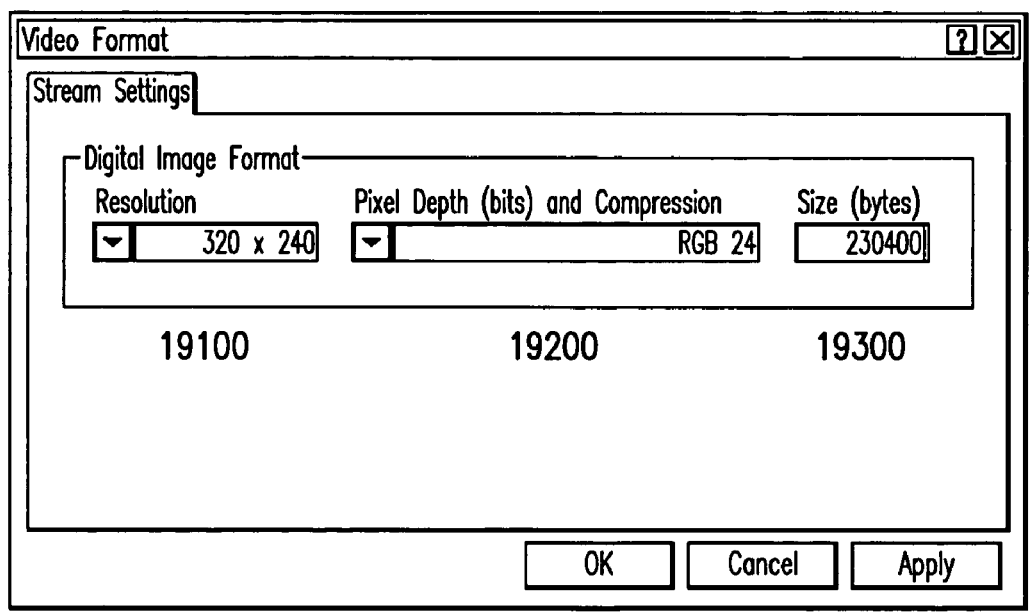
FIG. 19 is an exemplary user interface 19000.
Figure 20:
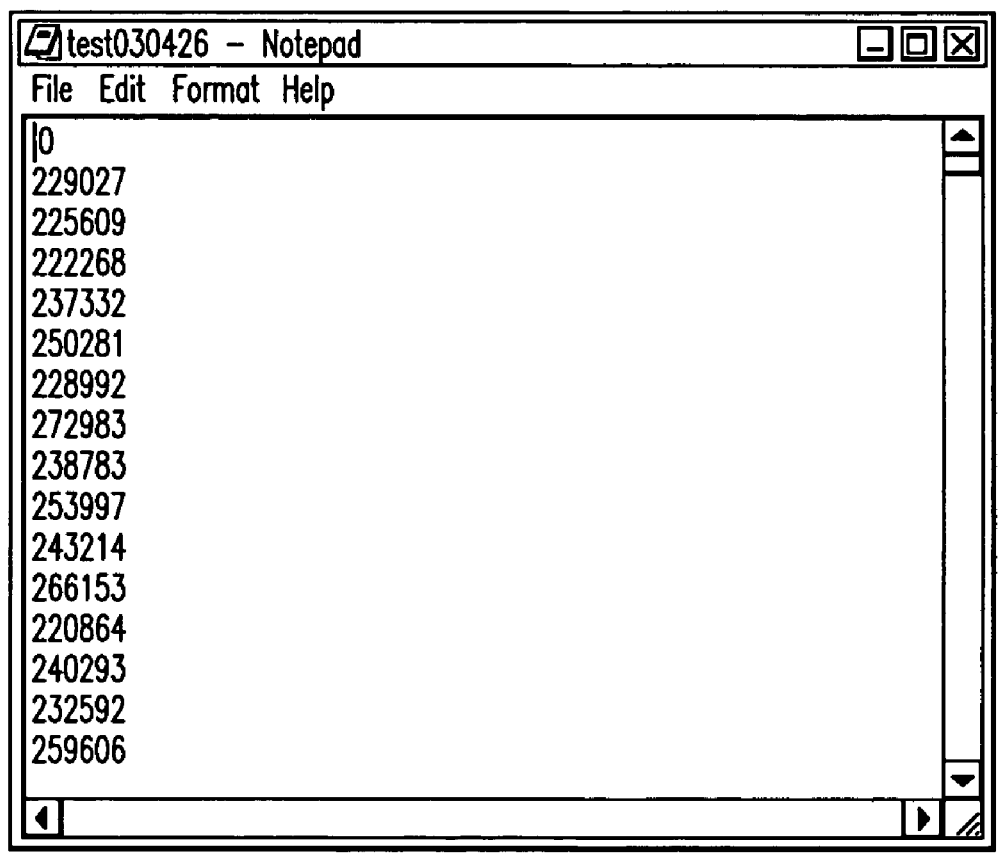
FIG. 20 is an exemplary output data list 20000.
Figure 21:
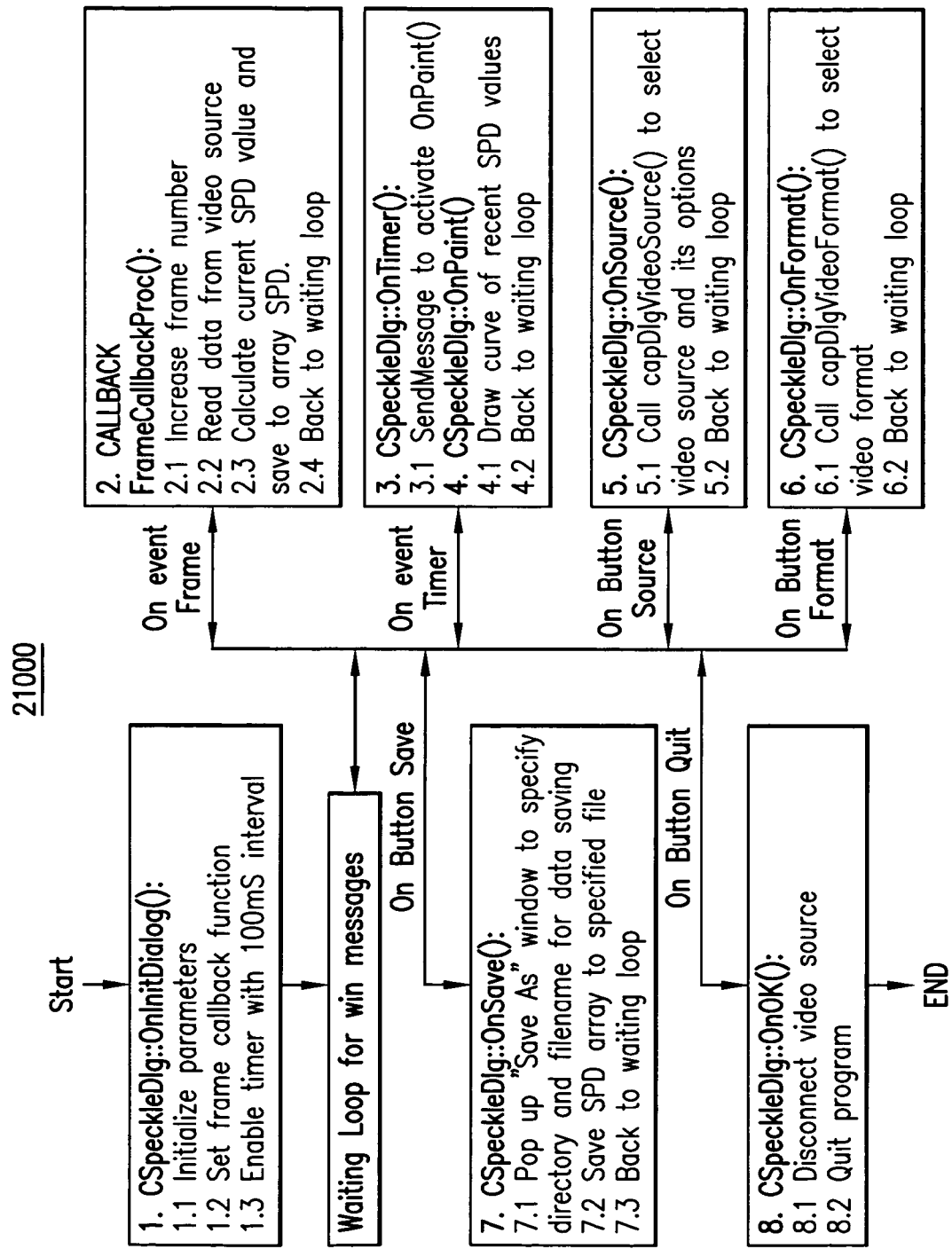
FIG. 21 is structural diagram of an exemplary software program 21000.

FIG. 19 is an exemplary user interface 19000 for stream settings. User interface 19000 can include a wide variety of user interface elements, such as indicators, selectors, and/or controls for resolution 19100, pixel depth and/or compression 19200, and/or size 19300, etc. FIG. 20 is an exemplary output data list 20000, which can display a plurality of SPD values 20100. FIG. 21 is structural diagram of an exemplary software program 21000.

Figure 22:
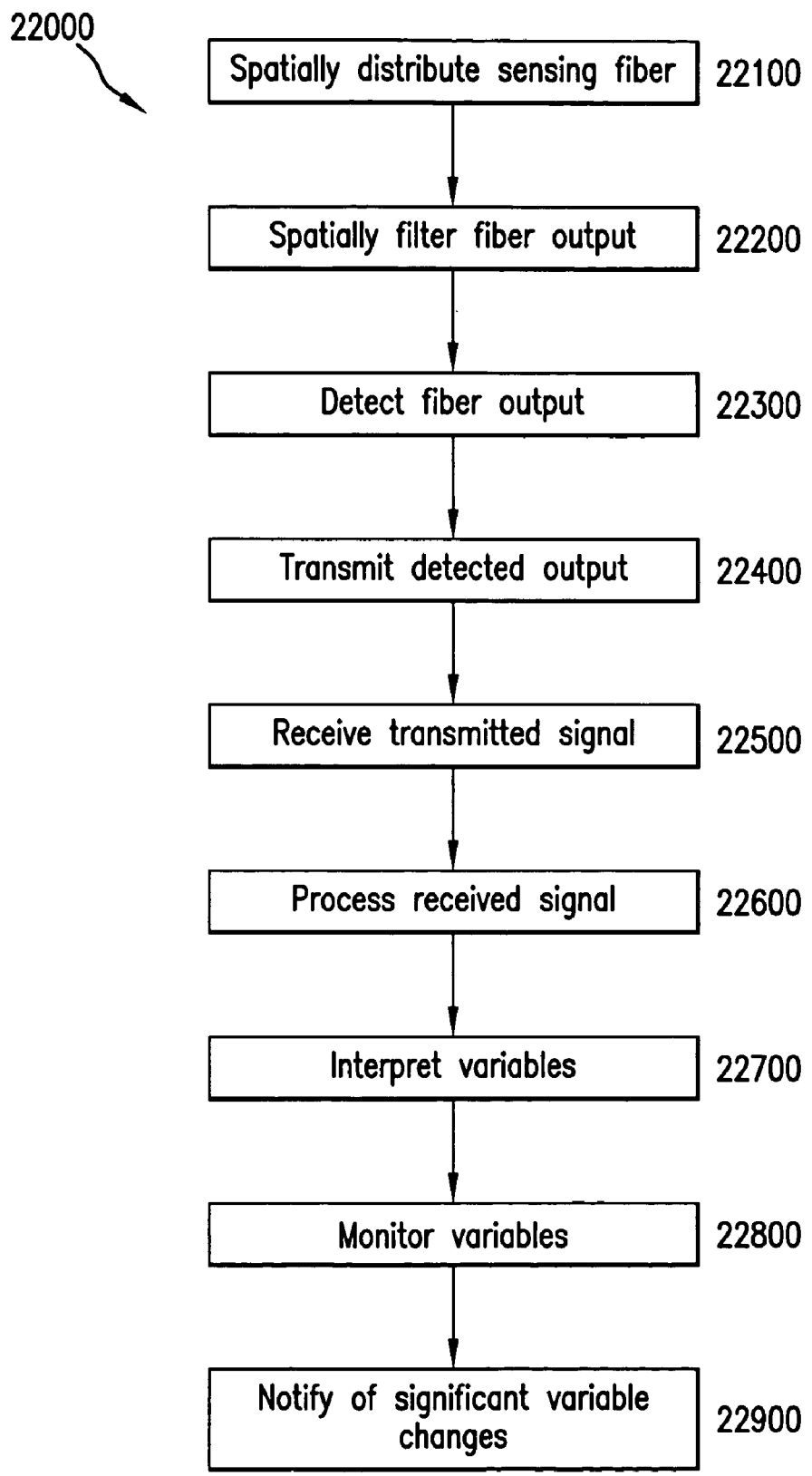
FIG. 22 is a flowchart of an exemplary embodiment of a method 22000.

FIG. 22 is a flowchart of an exemplary embodiment of a method 22000. At activity 22100, an optical fiber is spatially distributed in a predetermined pattern for facilitating sensing of a predetermined type of perturbation. For example, a fiber can be distributed on a bed in a pattern that is known to facilitate sensing of a person leaving or entering the bed, a position of the person on the bed, whether the person has rolled lately, a heartbeat of the person, and/or a respiration rate of the person, etc. A fiber can be distributed in a pattern that is known to facilitate sensing of a target, such as a person, animal, and/or vehicle, etc., entering an area and/or leaving the area. A fiber can be distributed in a pattern that is known to facilitate sensing of whether a perturbation is caused by a person, an animal, or an object, etc., potentially by virtue of a weight, weight distribution, and/or frequency of impact, etc. The presence of the fiber can be hidden and/or non-intrusive. The fiber can be rugged and/or impervious to liquid contact.

At activity 22200, output of the fiber can be spatially filtered. Such filtering can occur optically and/or digitally. At activity 22300, output of the fiber, such as optical signals, can be detected. At activity 23400, the detected fiber output can be transmitted, such as via an electro-magnetic signal, such as a wireless signal. Prior to transmission, the detected output can be formatted, source encoded, encrypted, channel encoded, multiplexed, modulated, and/or frequency spread, etc. At activity 23500, the transmitted signal can be received.

The receiver can receive signals from multiple transmitters. At activities 23600 and 23700, the received signal can be processed, which can include frequency despreading, demodulating, sampling, holding, digitizing, detecting, demultiplexing, channel decoding, decrypting, source decoding, synchronization, spatial filtering, comparing, summing, calculating, interpreting, and/or analyzing the signal and/or variables encoded therein. For example, the received signal can be processed to determine intensity, power, voltage, current, phase, and/or frequency values, and/or changes therein. Via time division, frequency division, code division, phase division, and/or other division techniques for multiple access and/or multiplexing, multiple signals can be received by a single receiver and/or processed by a single signal processor. Because a least certain such values of the signal can vary with time, particularly due to perturbations of the sensing fiber, at activity 22800, the signal, variable values, and/or received data can be continuously and monitored for statistically significant deviations from predetermined values and/or limits. At activity 22900, a notification can be provided if a deviation is detected. The notification can be provided by any technique and can be in any form. For example, a warning notification can be provided to a nurse if a patient has been immobile for too long and needs to be turned to prevent the formation of bed sores. As another example, a warning can be provided if motion is detected when, where, and/or to an extent not expected, such as for example, if the force, impact, and/or acceleration, etc., of a fallen patient, an intruder, an overweight truck approaching a bridge, seismic movement, and/or vibration, etc., is detected. Any or all detected, processed, monitored, and/or notification data can be logged. Thus, if a notification is provided to a nurse to turn a patient, the system can also log that the turn occurred, thereby providing a validation record of the movement to limit and/or avoid potential liability.

Figure 23:
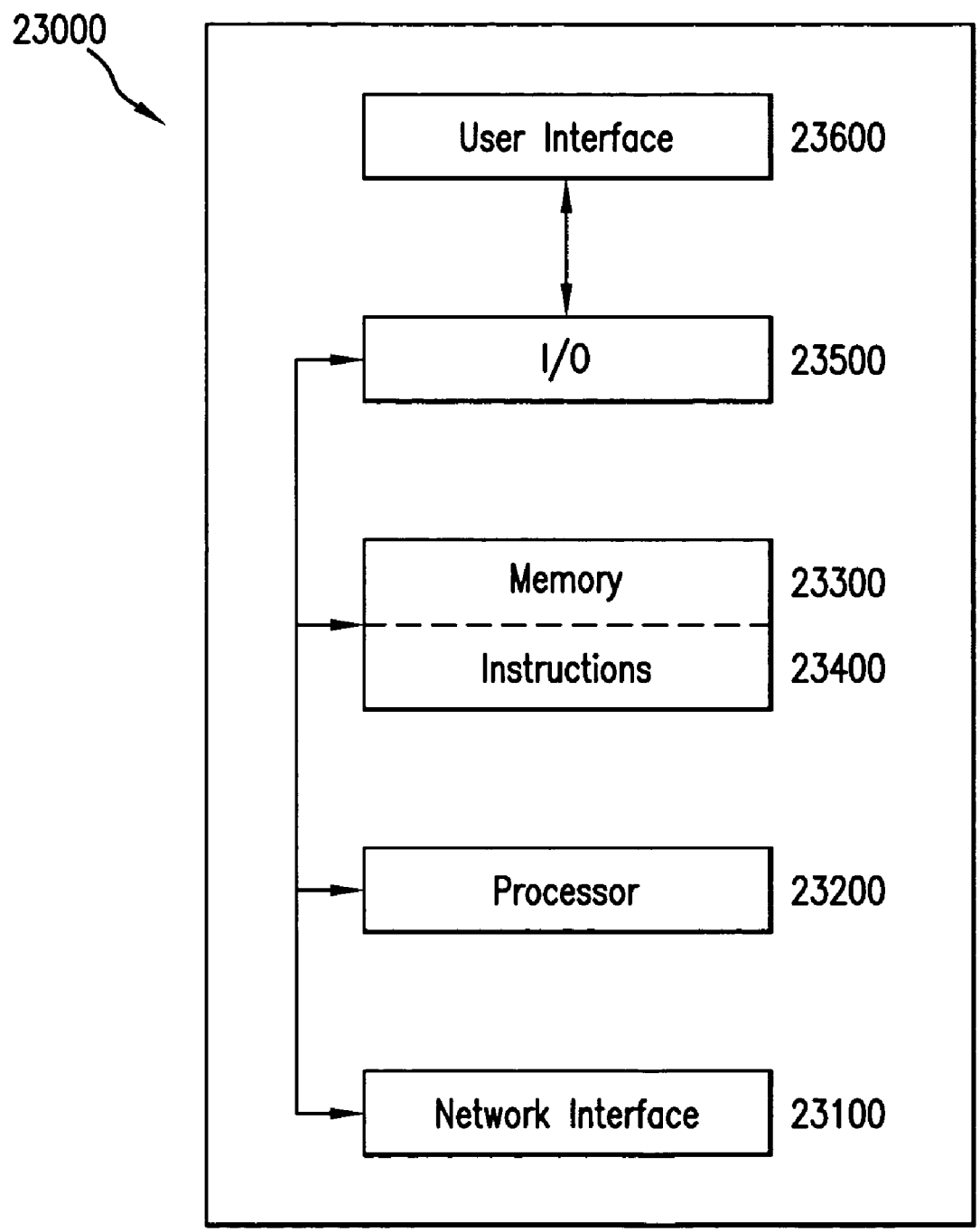
FIG. 23 is a block diagram of an exemplary embodiment of an information device 23000.

FIG. 23 is a block diagram of an exemplary embodiment of an information device 23000, which can represent any of information device described herein, such as information device 13900 of FIG. 13. Information device 23000 includes any of numerous well-known components, such as for example, one or more network interfaces 23100, one or more processors 23200, one or more memories 23300 containing instructions 23400, and/or one or more input/output (I/O) devices 23500, etc. Via one or more I/O devices 23500, a user interface 23600 can be provided.

As used herein, the term "information device" means any device capable of processing information, such as any general purpose and/or special purpose computer, such as a personal computer, workstation, server, minicomputer, mainframe, supercomputer, computer terminal, laptop, wearable computer, and/or Personal Digital Assistant (PDA), mobile terminal, Bluetooth device, communicator, "smart" phone (such as a Handspring Treo-like device), messaging service (e.g., Blackberry) receiver, pager, facsimile, cellular telephone, a traditional telephone, telephonic device, a programmed microprocessor or microcontroller and/or peripheral integrated circuit elements, an ASIC or other integrated circuit, a hardware electronic logic circuit such as a discrete element circuit, and/or a programmable logic device such as a PLD, PLA, FPGA, or PAL, or the like, etc. In general any device on which resides a finite state machine capable of implementing at least a portion of a method, structure, and/or or graphical user interface described herein may be used as an information device. An information device can include well-known components such as one or more network interfaces, one or more processors, one or more memories containing instructions, and/or one or more input/output (I/O) devices, one or more user interfaces, etc.

As used herein, the term "network interface" means any device, system, or subsystem capable of coupling an information device to a network. For example, a network interface can be a telephone, cellular phone, cellular modem, telephone data modem, fax modem, wireless transceiver, ethernet card, cable modem, digital subscriber line interface, bridge, hub, router, or other similar device.

As used herein, the term "processor" means a device for processing machine-readable instruction. A processor can be a central processing unit, a local processor, a remote processor, parallel processors, and/or distributed processors, etc. The processor can be a general-purpose microprocessor, such the Pentium III series of microprocessors manufactured by the Intel Corporation of Santa Clara, Calif. In another embodiment, the processor can be an Application Specific Integrated Circuit (ASIC) or a Field Programmable Gate Array (FPGA) that has been designed to implement in its hardware and/or firmware at least a part of an embodiment disclosed herein.

As used herein, a "memory device" means any hardware element capable of data storage, such as for example, a non-volatile memory, volatile memory, Random Access Memory, RAM, Read Only Memory, ROM, flash memory, magnetic media, a hard disk, a floppy disk, a magnetic tape, an optical media, an optical disk, a compact disk, a CD, a digital versatile disk, a DVD, and/or a raid array, etc.

As used herein, the term "firmware" means machine-readable instructions that are stored in a read-only memory (ROM). ROM's can comprise PROMs and EPROMs.

As used herein, the term "I/O device" means any sensory-oriented input and/or output device, such as an audio, visual, haptic, olfactory, and/or taste-oriented device, including, for example, a monitor, display, projector, overhead display, keyboard, keypad, mouse, trackball, joystick, gamepad, wheel, touchpad, touch panel, pointing device, microphone, speaker, video camera, camera, scanner, printer, haptic device, vibrator, tactile simulator, and/or tactile pad, potentially including a port to which an I/O device can be attached or connected.

As used herein, the term "haptic" means both the human sense of kinesthetic movement and the human sense of touch. Among the many potential haptic experiences are numerous sensations, body-positional differences in sensations, and time-based changes in sensations that are perceived at least partially in non-visual, non-audible, and non-olfactory manners, including the experiences of tactile touch (being touched), active touch, grasping, pressure, friction, traction, slip, stretch, force, torque, impact, puncture, vibration, motion, acceleration, jerk, pulse, orientation, limb position, gravity, texture, gap, recess, viscosity, pain, itch, moisture, temperature, thermal conductivity, and thermal capacity.

As used herein, the term "user interface" means any device for rendering information to a user and/or requesting information from the user. A user interface includes at least one of textual, graphical, audio, video, animation, and/or haptic elements. A textual element can be provided, for example, by a printer, monitor, display, projector, etc. A graphical element can be provided, for example, via a monitor, display, projector, and/or visual indication device, such as a light, flag, beacon, etc. An audio element can be provided, for example, via a speaker, microphone, and/or other sound generating and/or receiving device. A video element or animation element can be provided, for example, via a monitor, display, projector, and/or other visual device. A haptic element can be provided, for example, via a very low frequency speaker, vibrator, tactile stimulator, tactile pad, simulator, keyboard, keypad, mouse, trackball, joystick, gamepad, wheel, touchpad, touch panel, pointing device, and/or other haptic device, etc.

A user interface can include one or more textual elements such as, for example, one or more letters, number, symbols, etc. A user interface can include one or more graphical elements such as, for example, an image, photograph, drawing, icon, window, title bar, panel, sheet, tab, drawer, matrix, table, form, calendar, outline view, frame, dialog box, static text, text box, list, pick list, pop-up list, pull-down list, menu, tool bar, dock, check box, radio button, hyperlink, browser, button, control, palette, preview panel, color wheel, dial, slider, scroll bar, cursor, status bar, stepper, and/or progress indicator, etc. A textual and/or graphical element can be used for selecting, programming, adjusting, changing, specifying, etc. an appearance, background color, background style, border style, border thickness, foreground color, font, font style, font size, alignment, line spacing, indent, maximum data length, validation, query, cursor type, pointer type, autosizing, position, and/or dimension, etc. A user interface can include one or more audio elements such as, for example, a volume control, pitch control, speed control, voice selector, and/or one or more elements for controlling audio play, speed, pause, fast forward, reverse, etc. A user interface can include one or more video elements such as, for example, elements controlling video play, speed, pause, fast forward, reverse, zoom-in, zoom-out, rotate, and/or tilt, etc. A user interface can include one or more animation elements such as, for example, elements controlling animation play, pause, fast forward, reverse, zoom-in, zoom-out, rotate, tilt, color, intensity, speed, frequency, appearance, etc. A user interface can include one or more haptic elements such as, for example, elements utilizing tactile stimulus, force, pressure, vibration, motion, displacement, temperature, etc.

In certain exemplary embodiments, via one or more user interfaces 23600, a user can specify, input, view, locate, store, output, manipulate, and/or control, data, variables, parameters, and/or commands related to an operation of an optical sensing system, such as described herein.

Figure 24:
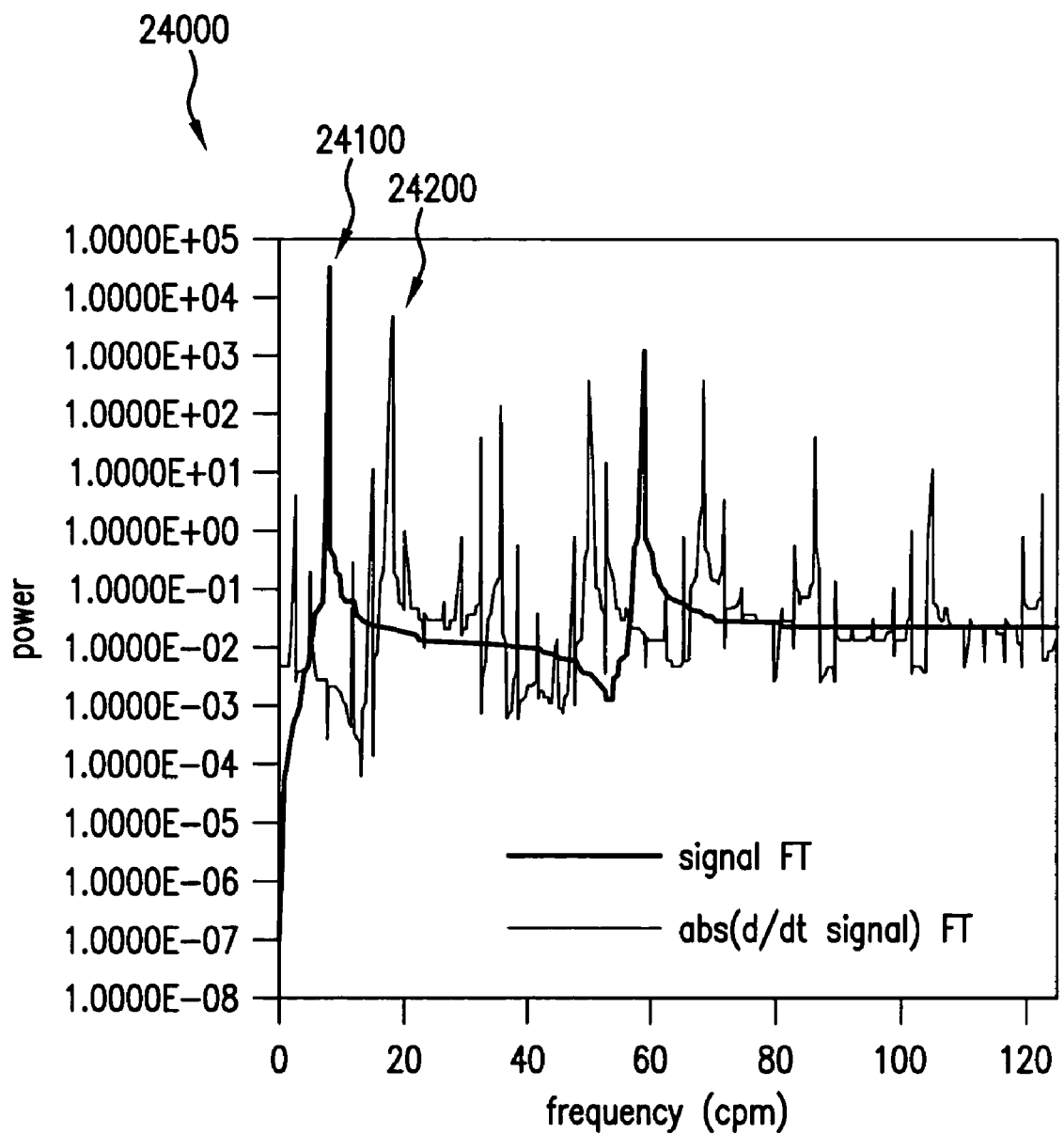
FIG. 24 is a plot of a power spectra of two exemplary perturbation detections.

We analyzed the applicability of these two techniques for simultaneously detecting patient movement, respiration and heart rate. The perturbation due to respiration and heart rate was modeled as the sum of two cosine functions with the second cosine having an amplitude of 0.1 of the amplitude of the first. The discrete Fourier transform of this modeled signal and the transform of the absolute value of the first derivative of the signal is shown in FIG. 24. As can be seen, the modeled SMS power spectra (fine line) clearly shows the first perturbation (at twice its frequency due to the taking of absolute value) but does not show the second perturbation due to complications from this type of processing. The HOME signal, on the other hand, clearly shows the peaks due to both perturbations at their correct frequencies. The SMS approach allows detection of respiration and heart rate and is more sensitive than the HOME approach, but the HOME approach introduces less distortion due to processing and should allow better signal discrimination.

Figure 25:
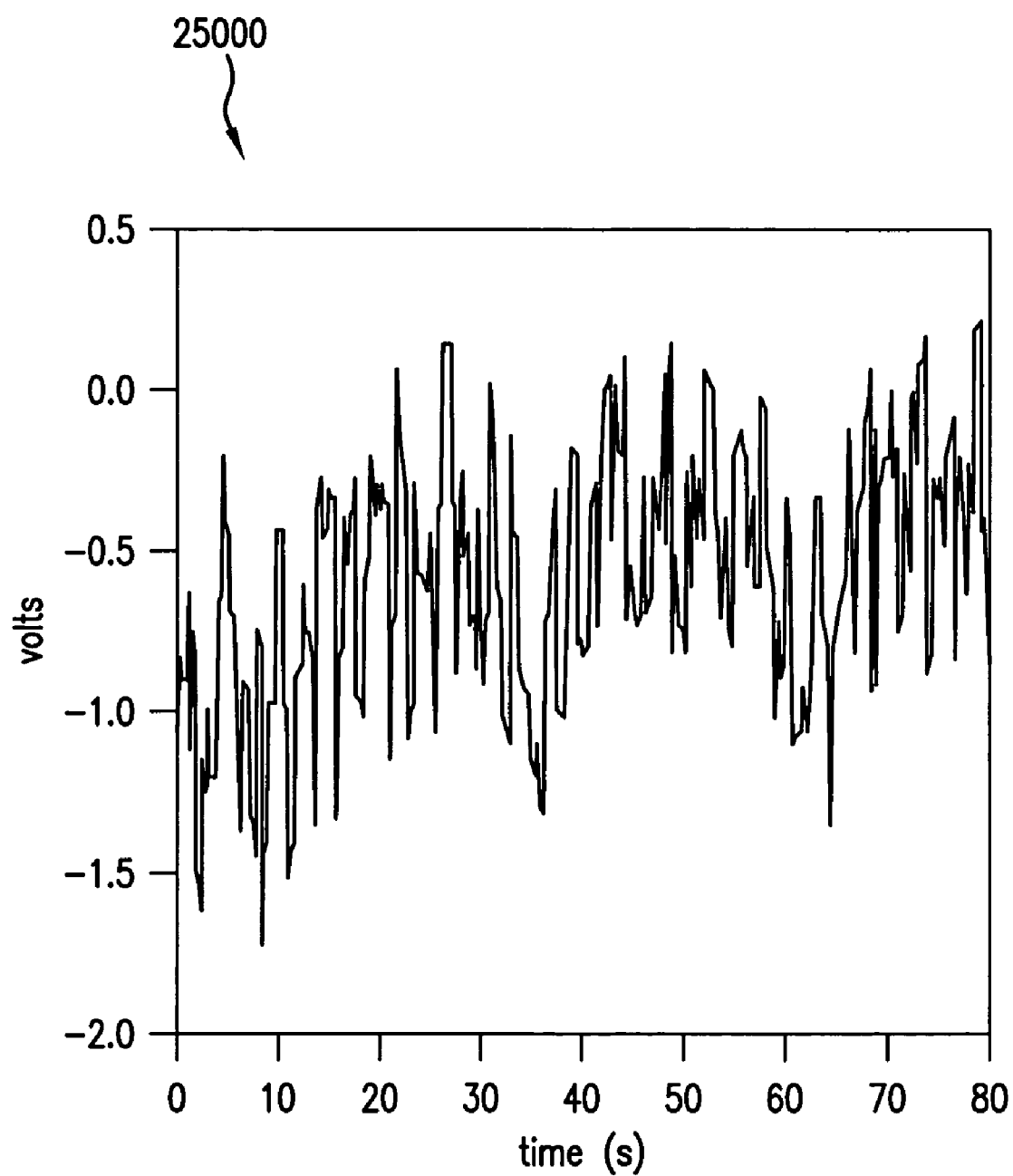
FIG. 25 is a plot of an exemplary time trace from an exemplary embodiment of an SMS sensor.
Figure 26:
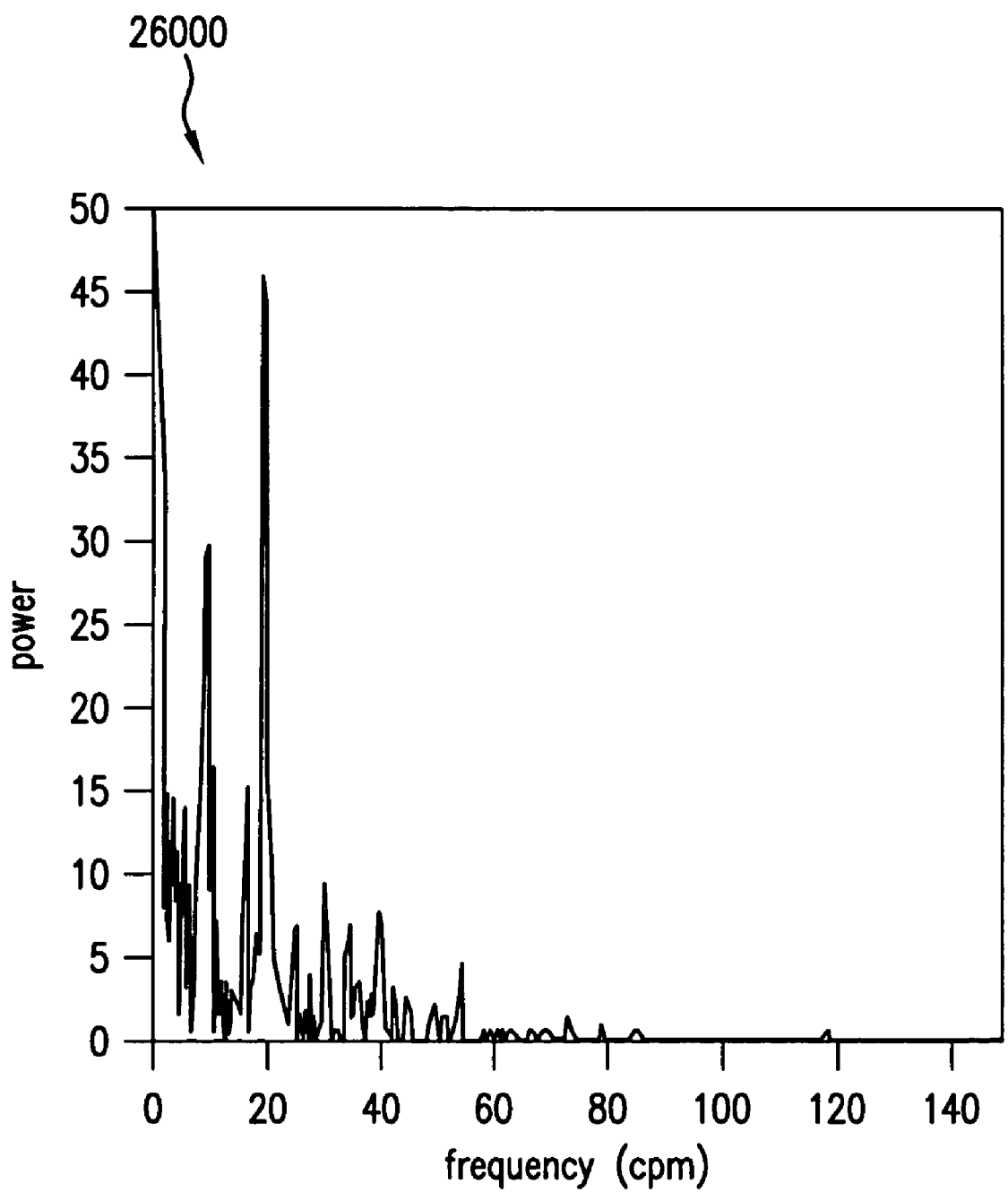
FIG. 26 is a plot of a power spectra of the signal of FIG. 25.
Figure 27:
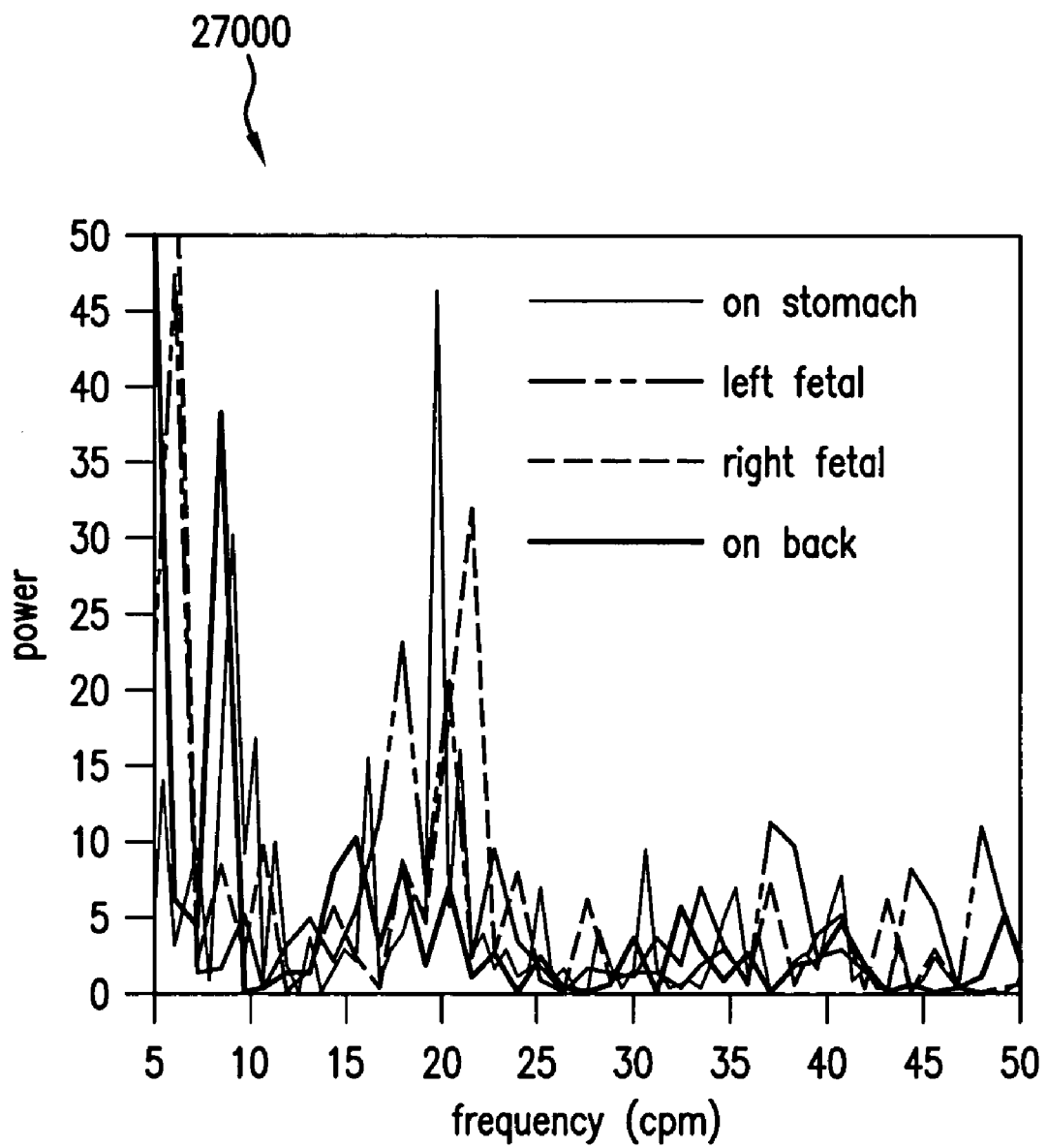
FIG. 27 is a plot of an exemplary power spectra for different positions.

A number of experimental runs were conducted using both the SMS and HOME sensors. A typical time trace from the SMS sensor is shown in FIG. 25 while its Fourier transform is shown in FIG. 26. FIG. 27 shows how the results vary for patients in different typical sleep positions:

on back, on stomach, left fetal and right fetal. The signal peaks are at twice the respiration rate as expected.

Figure 28:
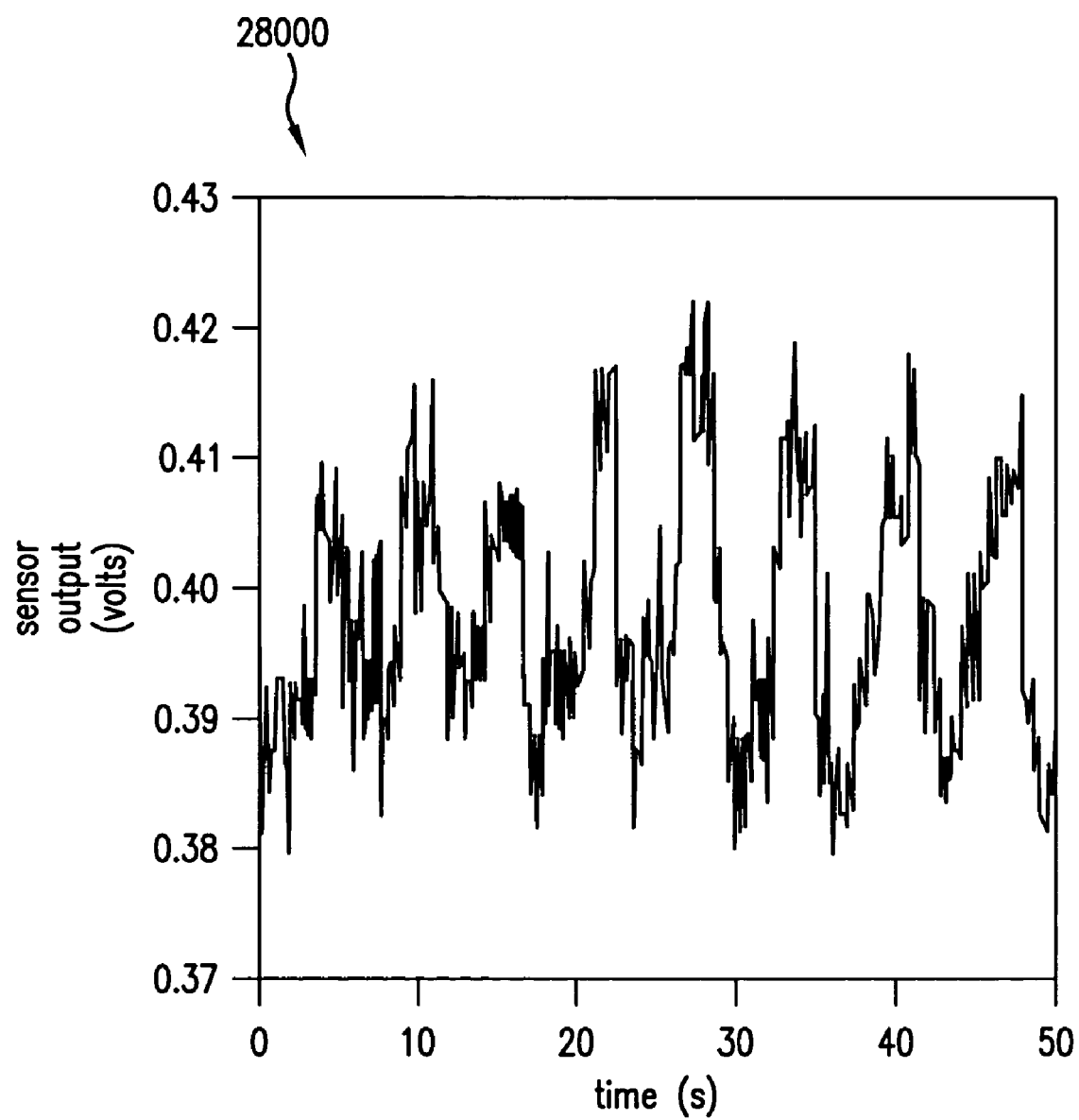
FIG. 28 is a plot of an exemplary time trace from an exemplary embodiment of a HOME sensor.
Figure 29:
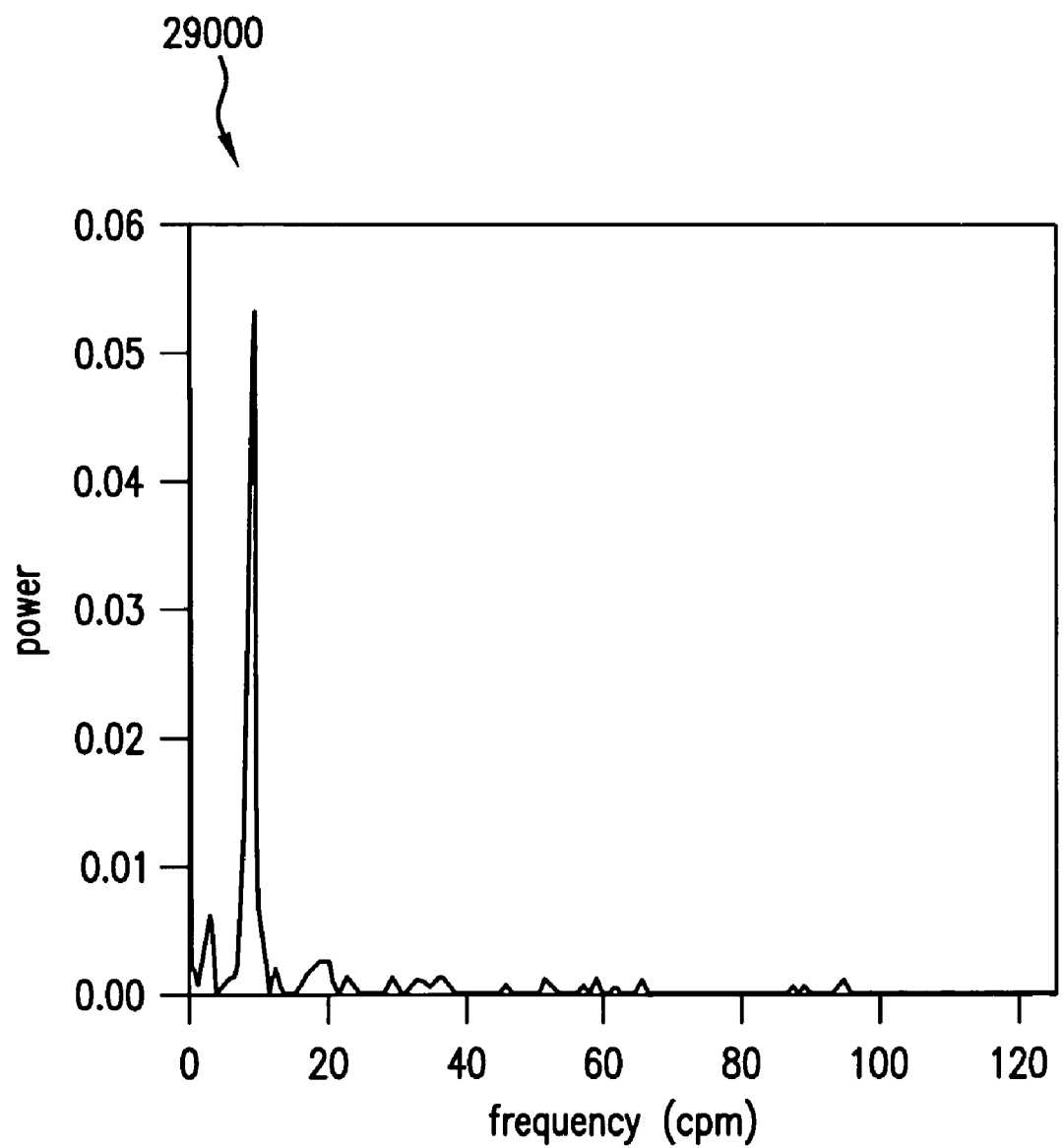
FIG. 29 is a plot of a power spectra of the signal of FIG. 28.

A typical time trace using the HOME sensor is shown in FIG. 28, and its power spectrum is shown in FIG. 29. FIG. 11 shows the power spectrum from the HOME sensor when the test subject held his breath for 0.5 of the measurement period. This allowed the heart rate signal to be clearly discerned. Finally, FIG. 12 displays the measured (via the peak in the power spectrum) vs the actual (as determined by patient counting) respiration rates using the HOME sensor.

As can be seen from these results, both the SMS and HOME sensors can be used to detect patient movement and respiration. Only the HOME sensor, however, demonstrated the ability to detect heart rate in this experiment. The SMS sensor, by the nature of its transduction process, will not become saturated, i.e. because it takes the derivative of a signal. The size of the DC component does not affect the sensitivity of this signal processing method. It can therefore detect patient movement and give repeatable results somewhat independently of patient weight. The HOME sensor, on the other hand, could be saturated by perturbations large enough to cause the available propagating mode volume to become completely filled. Both sensors can be low cost, PC compatible, and can be integrated into larger wireless systems.

Additional Embodiments 1

Certain exemplary embodiments combine two types of spatially integrating fiber optic sensors into a single sensor, potentially providing better performance than either one individually. In certain exemplary embodiments, coherent light passing through the sensing element, an extended multimode optical fiber, has its properties modulated by the integrated perturbation along the fiber. There are two modes of operation for the combined sensor, the first is a very sensitive optical interference approach that yields the absolute value of the first time derivative of the integrated perturbation. When perturbations saturate the sensor, the second mode of operation based on high order to low order mode conversion can be utilized to provide a direct measure of the integrated perturbation. The sensing element and preprocessing can take place at the sensing location while the actual processing can take place in a computer at a remote location connected wirelessly to the sensing element. The sensing element can be configured to optimally detect spatially varying parameter fields of interest. This "matched filtering" can be useful for a number of applications, such as:
- non-intrusive monitoring of patient activity and vital signs (smart bed);
- intrusion monitoring/physical activity (eldercare, fiber placed under carpets, etc.);
- illegal immigration detection (long sensing element placed along border);
- rapid deployment perimeter violation detection (military, security/homeland security applications);
- structural health monitoring (vibration/perturbation response detection);
- seismic monitoring (earthquakes, nuclear tests, explosions); and/or
- active control systems (aircraft, spacecraft, ships, submarines); etc.

Certain exemplary embodiments can provide an optical fiber-based, distributed vibration sensor that can utilize two distinct spatial mode detection techniques to extend the overall dynamic range and/or detection capabilities of the system. The system can employ a laser diode source, a multimode optical fiber sensor, and/or a CCD camera. The more sensitive detection technique can be based on monitoring changes in the speckle pattern due to modal interference. The system can be used to non-invasively monitor patient vital signs, motion, and/or overall health.

In clinical settings such as hospitals, outpatient surgery centers, or nursing homes, vital signs such as pulse and respiratory rates typically are measured by direct observation by skilled medical personnel. Continuous monitoring of vital signs typically requires attachment of sensors to the body in a number of ways. Monitoring of essential vital signs typically is an integral part of medical care. Pulse rate can be determined by placement of electrodes on the skin and monitoring of the electrocardiogram. The output of a fiber optic sensor placed on a finger, toe, or ear lobe and attached to a pulse oximeter can be used to determine pulse rate. Respiratory rate can be determined by chest movement as detected by changes in chest wall electrical impedance or inductance. Each method for detecting pulse or respiration typically requires an interface between the sensor and the patient's skin and the sensor typically must be held in place with an adhesive or by mechanical means such as Velcro. Any of these sensors can cause skin irritation or breakdown and can contribute to patient discomfort.

Yet, these parameters can be useful for determining patient condition and/or preventing future problems for patients. Measurement of respiration rate and/or heart rate can provide immediate indication of whether a patient is in distress, while the measurement of patient movement can be used to determine whether patient movement has been so limited over a period of time that the patient must be turned to a new position by a health care professional, to prevent the occurrence and/or exacerbation of pressure sores (also known as "bed sores"). Pressure sores are a major cause of morbidity and mortality in the healthcare setting. As many as 1.5 million individuals are affected by pressure sores, at a total cost of 5 billion dollars annually. The prevalence of pressure sores in one US teaching hospital was 8%. Repositioning schedules are utilized as part of most preventive measures in healthcare facilities. Typical recommendations are for repositioning bed ridden patients every 2 hours and individuals in chairs at least once per hour. Thus, to help prevent pressure sores, it can be useful to monitor and/or document patient movements and/or repositionings.

In certain exemplary embodiments, two different techniques for sensing patient respiration rate and motion are utilized. Both techniques can rely on modulation of the modal distribution in multimode optical fibers and can be implemented on a single sensor platform.

Figure 30:
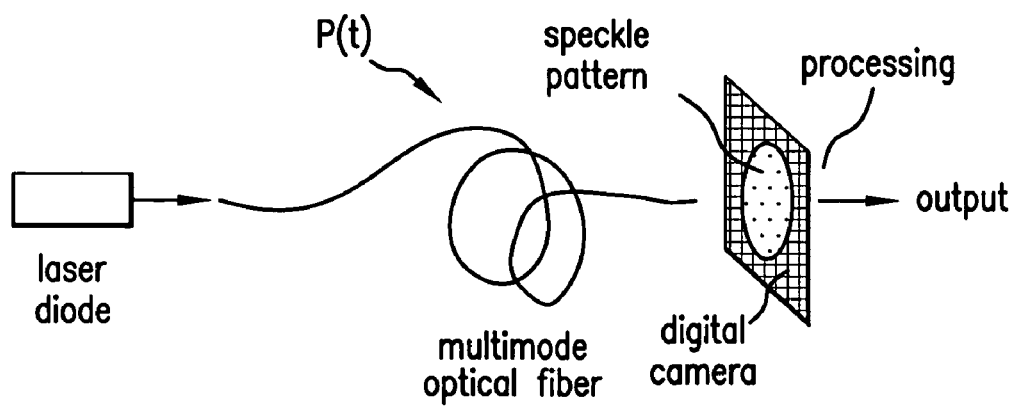
FIG. 30 is a block diagram of an exemplary embodiment of a system comprising a statistical mode (STM) sensor.

In certain exemplary embodiments, a spatially distributed integrating approach is utilized so that if a patient were present anywhere within a specific localized area, sensing could be carried out. The basic concept is that any patient movement that also moved an optical fiber within the specified area can produce a change in optical signal that can indicate patient movement. Physical repetitive movement caused by respiration or heart pumping can be contained within the signal as well and can be extracted via appropriate signal processing. To test this concept, two different modal modulation approaches were used with a multimode optical fiber excited by a coherent laser source. In the first technique (called statistical mode sensing or STM), all the guided modes of the fiber can be excited and then detected by a low cost digital camera. This is shown schematically in FIG. 30. The sum of the absolute values of the change in light intensity on each of the pixels between each time frame then can be calculated. This technique then can provide a measure of the absolute value of the first time derivative of a perturbation integrated along the fiber length.

Figure 31:
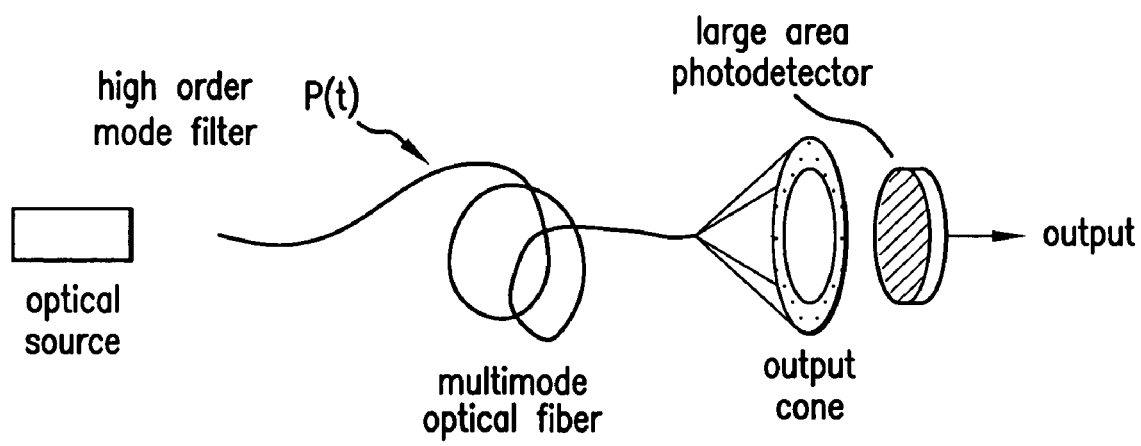
FIG. 31 is a block diagram of an exemplary embodiment of a system comprising a high order mode excitation (HOME) sensor.

In the second approach (called high order mode excitation or HOME), only the higher order modes of the fiber are excited so that the output from the unperturbed fiber can result in a bright annulus when projected on a screen. A large area circular photodetector can be positioned so that its diameter fits within the annulus but does not intercept it. A schematic diagram of this technique is shown in FIG. 31. When the fiber is perturbed, the perturbation can couple light from the higher order modes to lower order modes where it can be intercepted by the large area detector, converted into an electrical current and measured. This technique can provide a signal that can be directly proportional to the perturbation integrated along the fiber length.

We analyzed the applicability of these two techniques for simultaneously detecting patient movement, respiration and heart rate. The perturbation due to respiration and heart rate was modeled as the sum of two cosine functions with the second cosine (representing the perturbation due to the heart) having an amplitude of 0.1 relative to the amplitude of the first cosine (representing the perturbation due to respiration). The frequency of the second cosine had a frequency of 60 cycles/minute while the frequency of the first cosine was 9 cycles/minute. The frequencies were chosen to have roughly the same values as average respiration and heart rates, while the difference in amplitudes was chosen simply to represent the fact that physical body movement due to respiration typically is much greater than that due to heart action.

Figure 32:
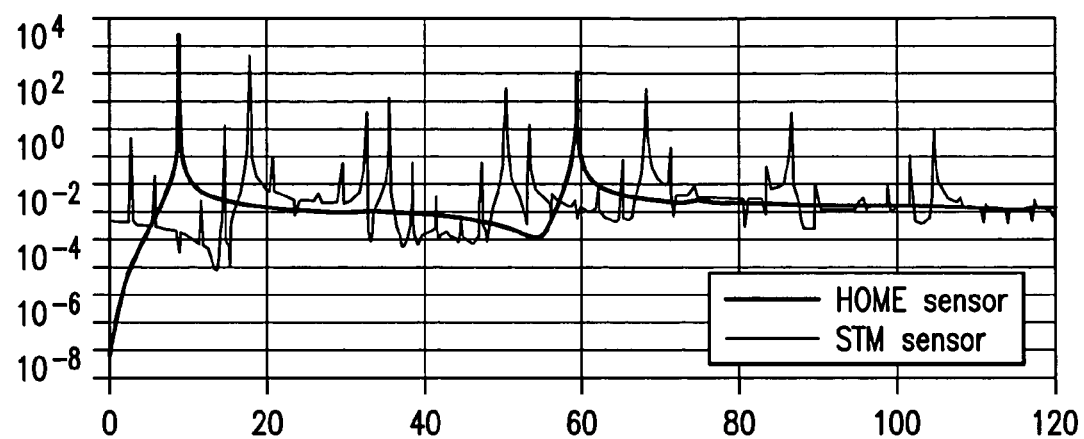
FIG. 32 is an exemplary modeled power spectra (arbitrary amplitude units vs. cycles/minute) of two perturbation detection by exemplary STM and HOME sensors.

This model can be considered a crude approximation, since the integrated perturbations due to the two sources (heart and lungs) would likely be periodic signals whose shapes would not be uniform in the same way mathematical cosine signals would be. Nonetheless, implementing the model was instructive as a way to contrast the two sensing techniques and the information they might be able to provide. The discrete Fourier transform of the modeled signal (sum of the two cosines, i.e. representing the HOME sensor), and the discrete Fourier transform of the absolute value of the first derivative of the modeled signal (representing the STM sensor) are shown in FIG. 32. One would expect that the power spectrum of the HOME sensor would show two clear peaks at the frequencies of the two cosine functions, since its output should be directly proportional to the modeled integrated perturbation. The power spectrum of the STM sensor, however, should be more complex. The fact that the processing takes an absolute value of the first time derivative of the integrated perturbation should produce signals with a maximum component at twice the fundamental frequencies and a distorted power spectrum (e.g., if one takes the absolute value of a cosine function, the frequency doubles and a discontinuity in the slope is introduced). This implies that large signals seen by the STM sensor at low frequencies will likely produce power spectra that mask the power spectra of signals at higher frequencies.

As can be seen from FIG. 32, the modeled STM power spectra (fine dashed line) shows the first cosine function (at twice its frequency due to the taking of absolute value) but does not clearly indicate the second cosine function due to the complications introduced by the sensor signal processing. The HOME signal, on the other hand, shows the peaks due to both perturbations at their correct frequencies. This suggests that the STM approach should show detection of respiration and perhaps heart rate, but the HOME approach should introduce less signal distortion due to processing and show better signal discrimination. It should also be noted that the HOME sensor output would likely saturate when sufficiently large levels of perturbation are present and the modal volume is uniformly populated, while the STM sensor should be relatively insensitive to saturation since it is based on interference.

Experiment

In order to develop a nonintrusive method of detecting respiration, heart rate, and patient movement, the top surface of a mattress was covered with a 200 micrometer core step index silica multimode optical fiber arranged in two sinusoidal overlapping patterns arranged orthogonal to each other so that the fiber in each pattern crossed the fiber in the other pattern at an angle of 90 degrees. Light from a laser pointer with output at 670 nanometers was used to excite the fiber and the output light was detected either by a digital camera or a large area photodetector depending upon the sensing technique used.

Results

Figure 33:
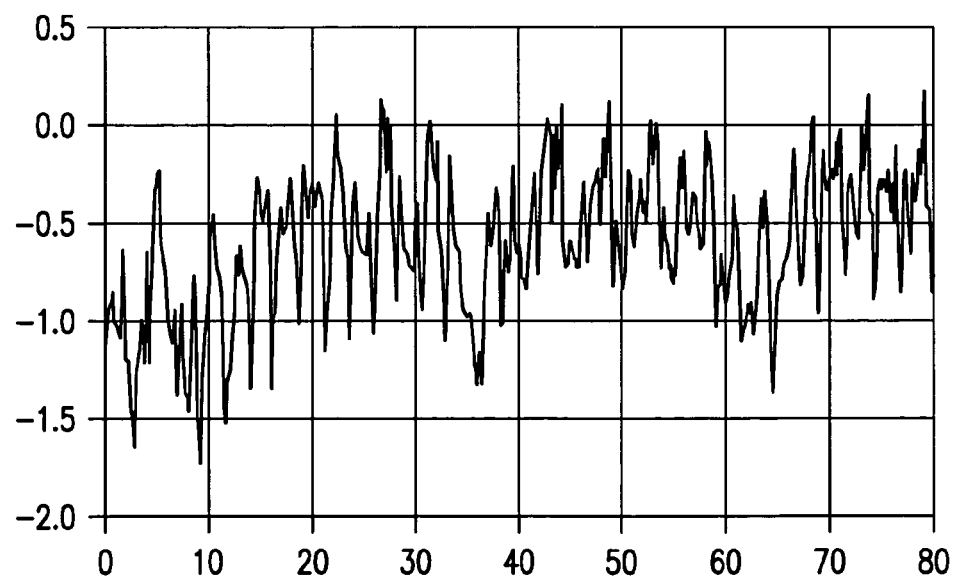
FIG. 33 is an exemplary typical time trace (arbitrary amplitude units vs. time (seconds)) from an exemplary STM sensor.
Figure 34:
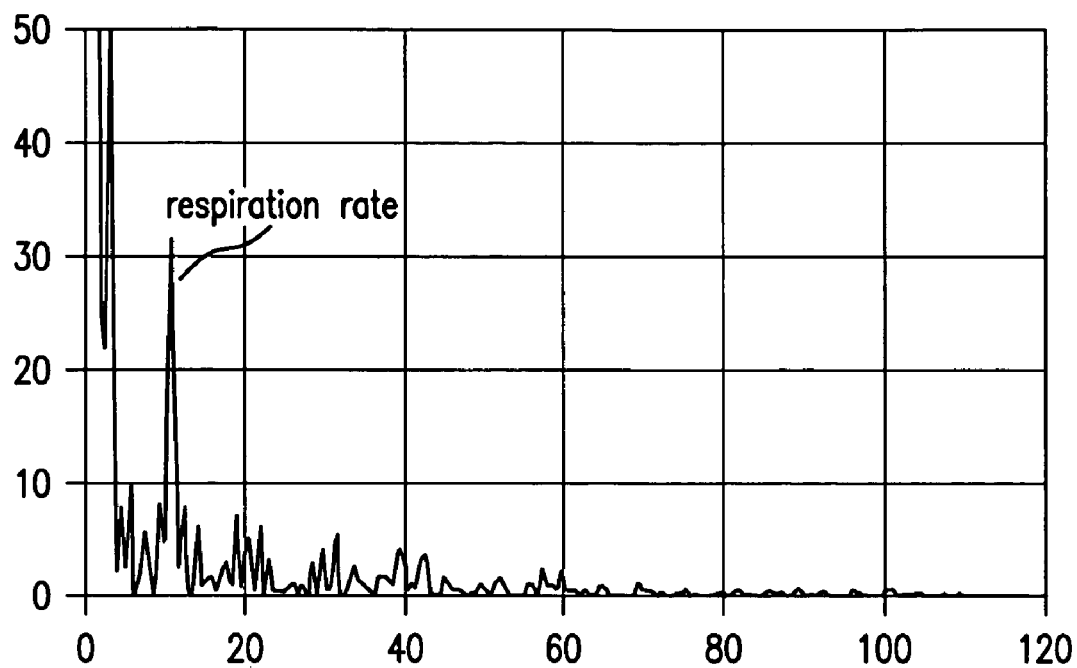
FIG. 34 is an exemplary power spectrum (arbitrary amplitude units vs. 0.5×counts/minute) of the time trace shown in FIG. 33.
Figure 35:
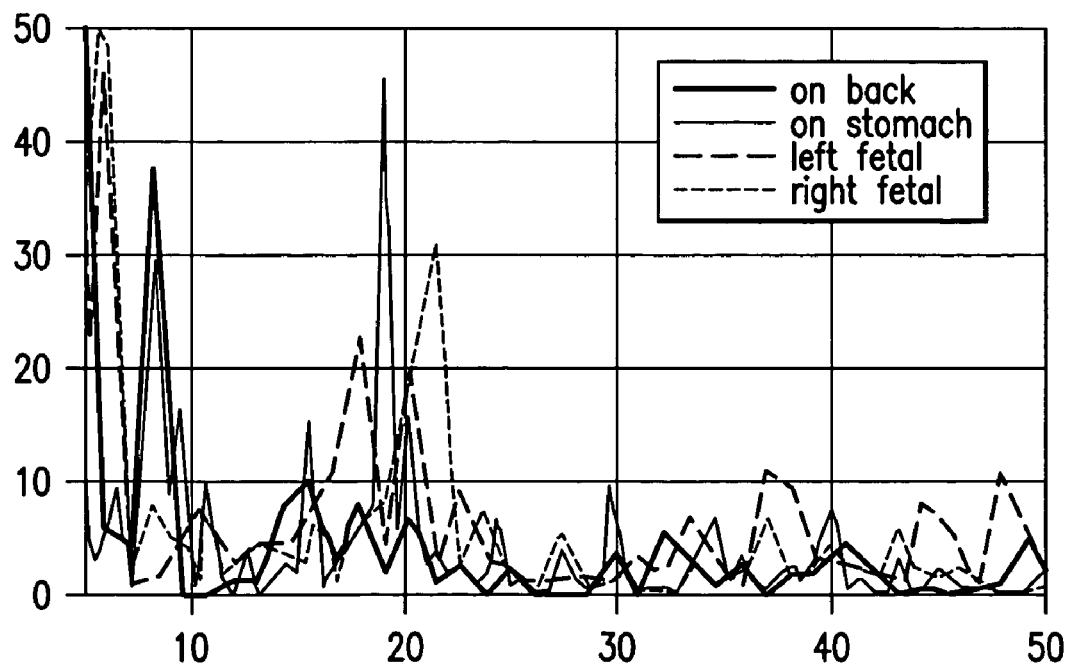
FIG. 35 is an exemplary STM sensor power spectra (arbitrary amplitude units vs. cycles/minute) for different test subject positions.

A number of experimental runs were conducted using both the STM and HOME sensors. Since the natural time intervals for measurements of physiological parameters are typically fractions of minutes (respiration rates are of the order of 10/minute and heart rates are of the order of 70/minute), most data is plotted against a time scale of minutes or cycles/minute. For perturbations due to a female test subject (height 1.6 m, mass 50 kg), a typical time trace from the STM sensor taken while the subject was lying on her stomach on the bed is shown in FIG. 33 while its Fourier transform is shown in FIG. 34. FIG. 35 shows how the results vary for the same test subject in different typical sleep positions: on back, on stomach, left fetal, and right fetal. The signal peaks are at twice the respiration rate as expected due to the absolute value taken during signal processing so that plotting the power spectra vs. 0.5 times the measured frequency provides the actual perturbation frequency values.

Figure 36:
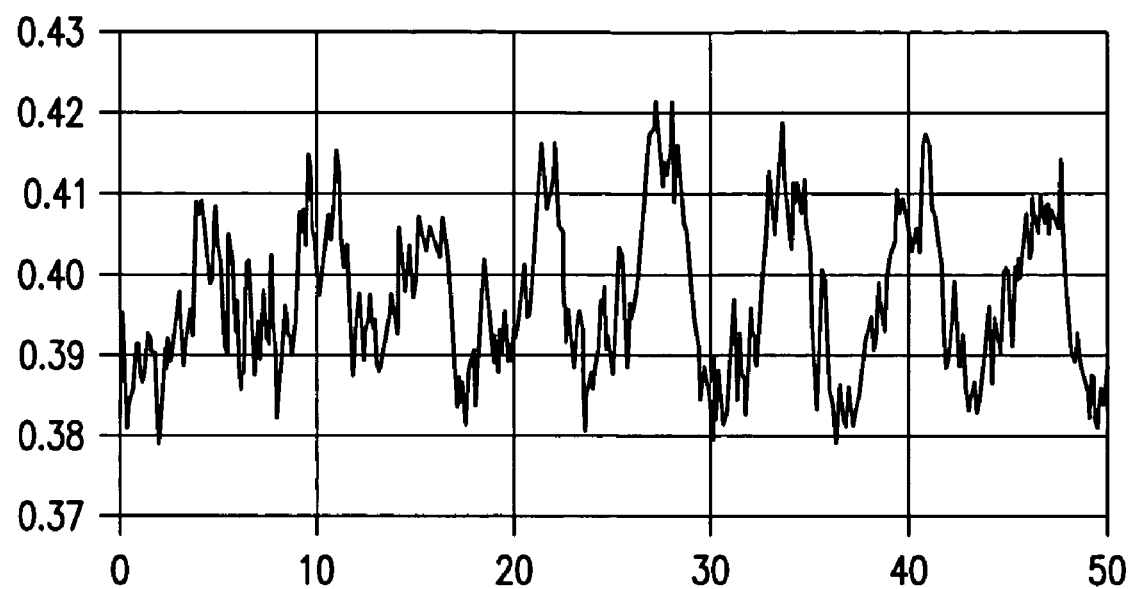
FIG. 36 is an exemplary typical time trace (arbitrary amplitude units vs. time (minutes)) from an exemplary HOME sensor.
Figure 37:
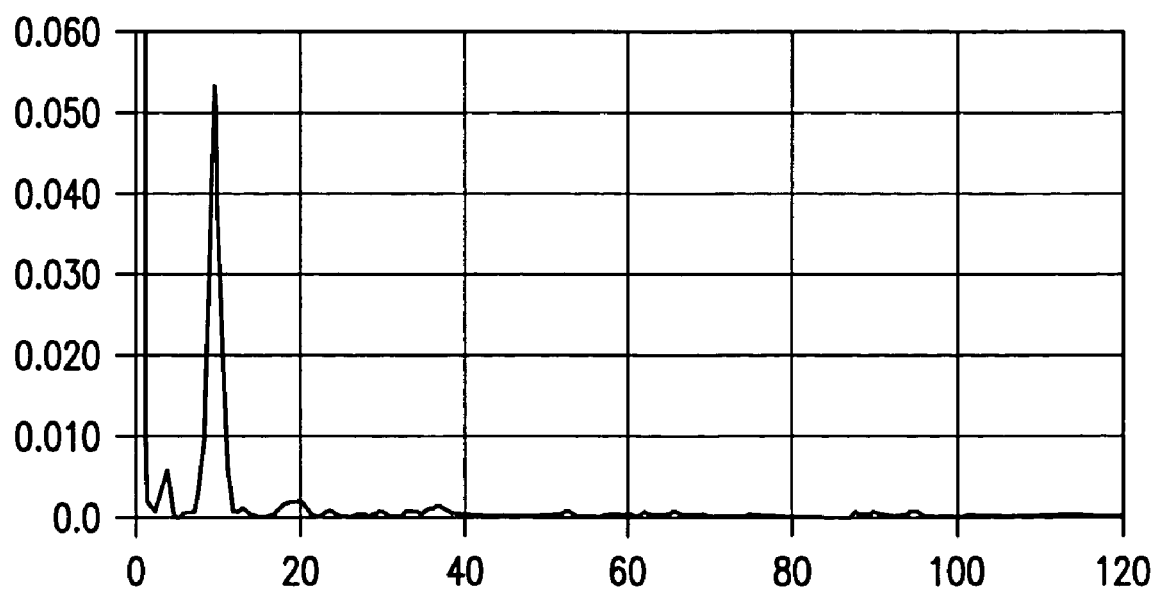
FIG. 37 is an exemplary power spectrum (arbitrary amplitude units vs. cycles/minute) of the time trace shown in FIG. 36.
Figure 38:
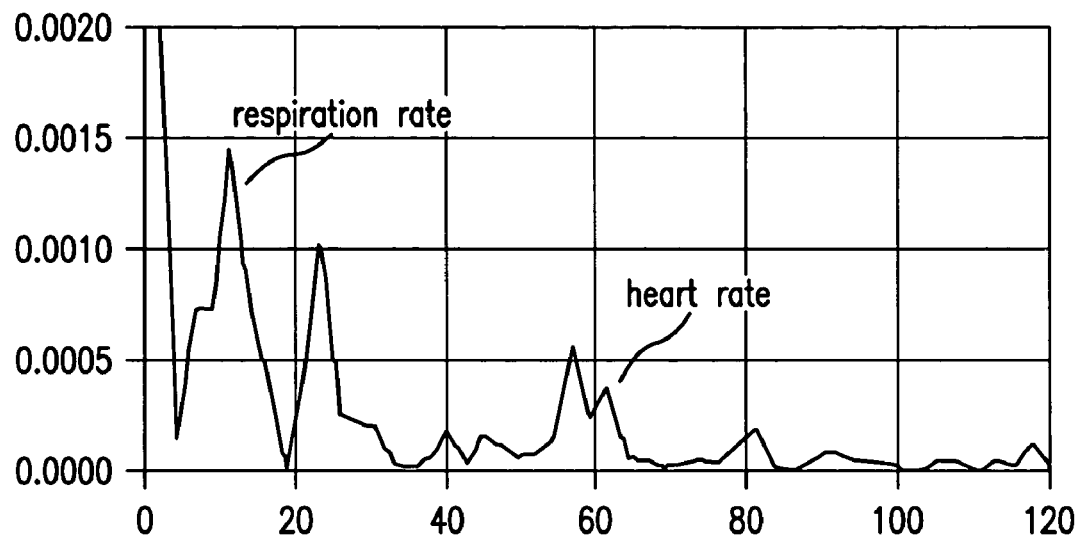
FIG. 38 is an exemplary HOME sensor power spectrum (arbitrary amplitude units vs. cycles/minute) showing breathing and heart rates.

For perturbations due to a male test subject (height 1.75 m, mass 80 kg) lying on his stomach on the bed, a typical time trace using the HOME sensor is shown in FIG. 36, and its power spectrum is shown in FIG. 37. FIG. 38 shows the power spectrum from the HOME sensor when the test subject held his breath for 0.5 of a measurement period. This allowed the heart rate signal to be clearly discerned although the respiration rate signal was distorted. Finally, FIG. 39 displays the measured (via the peak in the power spectrum) vs. the actual (as determined by patient counting) respiration rates using the HOME sensor.

Figure 39:
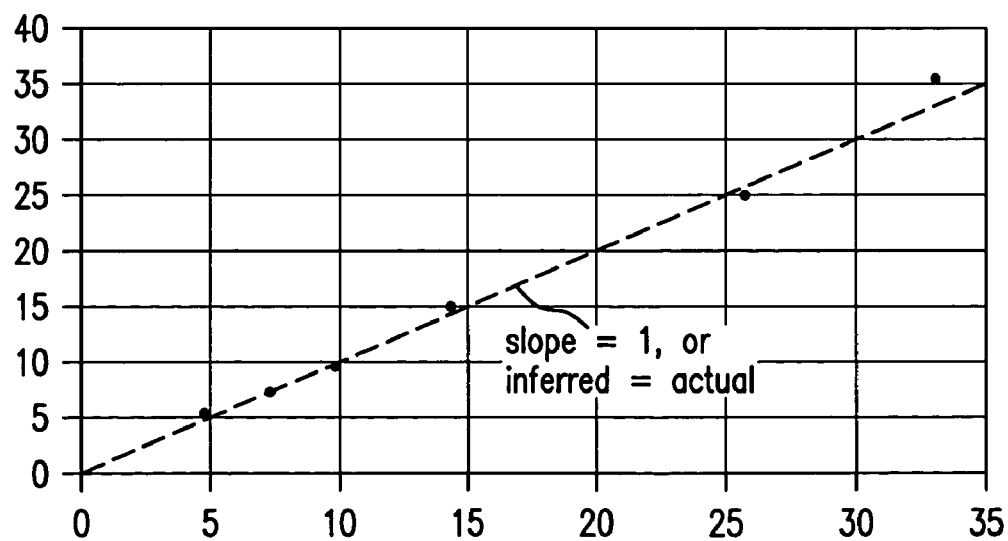
FIG. 39 is an exemplary plot of measured vs. actual breathing rates (cycles/minute (inferred)vs. cycles/minute (actual)) using an exemplary HOME sensor.

The results indicate that both the respiration rate and heart rate are represented in the signal although unusual measures needed to be taken (suppression of the respiration signal for half of a measurement period) to clearly show the heart rate signal in the power spectrum (FIG. 39). The signal is not clearly evident in FIG. 38 when the perturbation clue to respiration is not suppressed. It is believed that the introduction of a discontinuity in the respiration perturbation also resulted in an accentuation of its first harmonic in the power spectrum (the large signal at 24 cycles/minute which is clearly twice the frequency of the fundamental respiration rate, 12 cycles/minute) as shown in FIG. 39.

Figure 40:
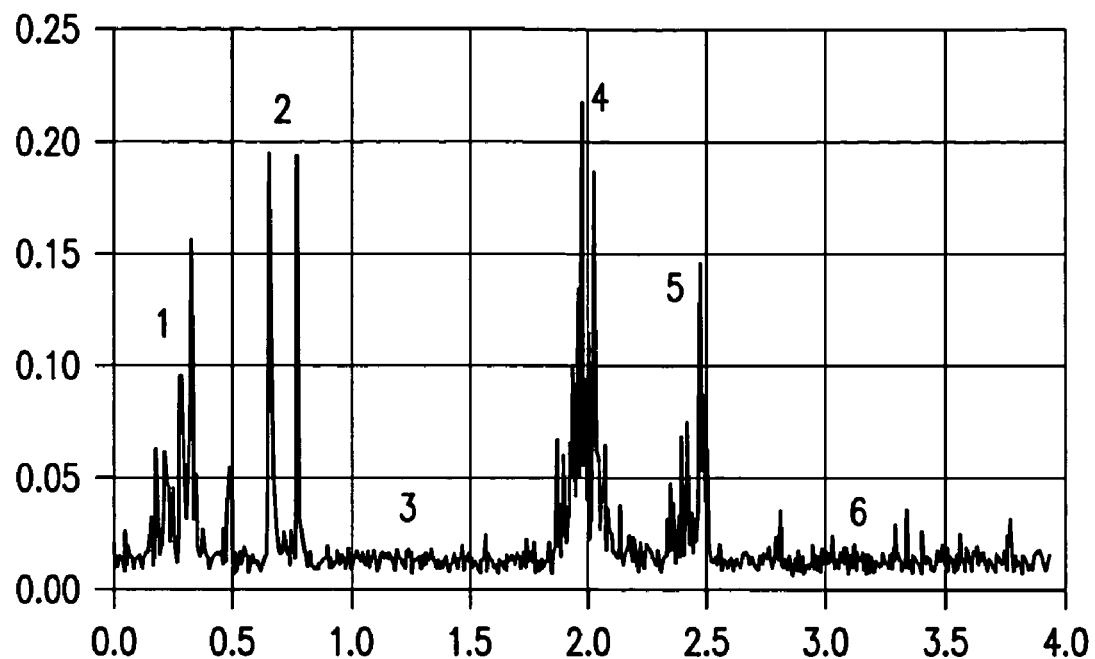
FIG. 40 is an exemplary STM sensor output (arbitrary amplitude units vs. time (minutes)) corresponding to a patient getting out of bed and then returning.
Figure 41:
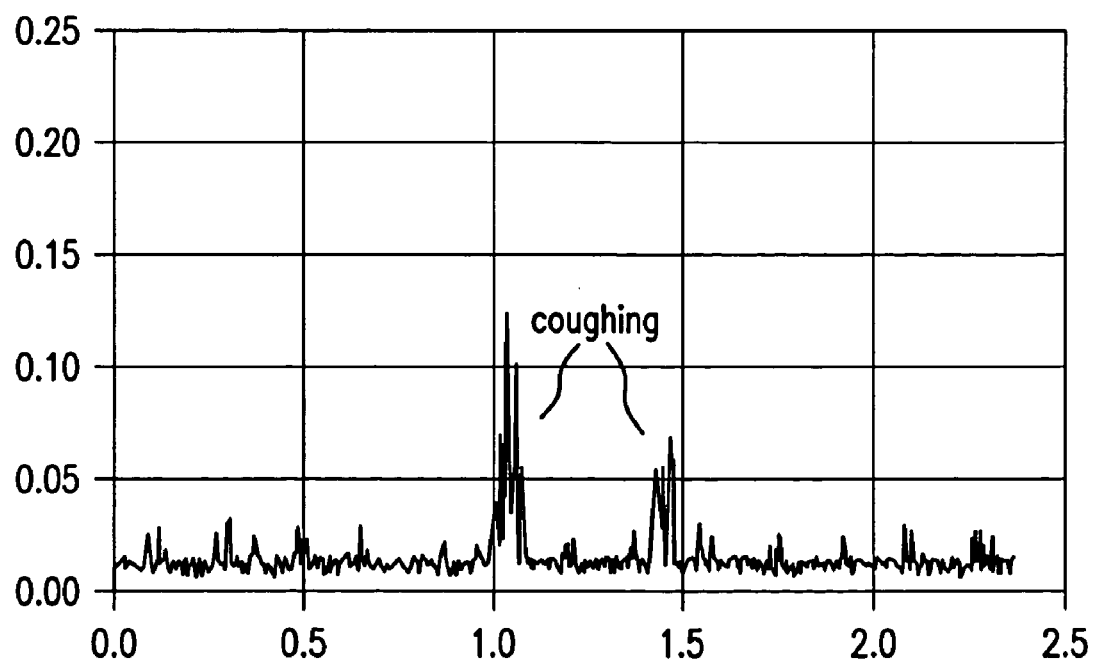
FIG. 41 is an exemplary STM sensor output (arbitrary amplitude units vs. time (minutes)) corresponding to a patient coughing.

A one night validation of the STM sensor was carried out at the Carilion Health System Sleep Center with an individual patient prior to the actual clinical trial. In FIG. 40, the output of the STM sensor is shown for a period of time when the patient moved to the edge of the bed (1), got up out of bed (2) leaving the bed empty (3), then sitting back down on the bed (4), settling to a comfortable position (5) and then resting quietly (6). In FIG. 41, the STM sensor response to a person coughing is clearly shown. These results clearly indicate the potential for nonintrusive patient measurement in the health care environment.

Discussion

As can be seen from these results, both the STM and HOME sensors can be used to detect patient movement and respiration. Only the HOME sensor, however, demonstrated the ability to dearly detect heart rate. These two sensors might have different applications. The STM sensor, by the nature of its transduction process, likely will not become saturated, i.e., the speckle pattern will always be present and will always change in response to additional perturbation. The size of the DC component does not affect the sensitivity of this signal processing method. It can therefore detect patient movement and give repeatable results that are somewhat independent of patient weight.

The HOME sensor, on the other hand, can be saturated by perturbations large enough to cause the available propagating mode volume to become completely filled. For applications involving critical care, the HOME sensor could find extensive application if a method can be found to make it more sensitive to heart rate. Both sensors offer the potential to be low cost, PC compatible, and have the capability to be integrated into larger wireless systems.

The outputs from the sensors integrated into the bed allow continuous monitoring of indications of patient movement, respiration rate and heart rate. These signals are all combined and typically are separated via signal processing. The smart bed can be a cost effective way of automating long term monitoring of patients that would enhance the productivity of health care professionals and optimize their one-an-one interaction time with those patients for whom the need for such personal interaction has become critical.

Certain exemplary embodiments can apply advanced signal processing techniques, such as Kalman filtering, to the outputs of the smart bed sensors. Our research has clearly shown that components due to the physiological parameters of interest are present in the sensor output signals.

Additional Embodiments 2

Certain exemplary embodiments can provide an optical fiber-based, distributed vibration sensor that can utilize two distinct spatial mode detection techniques to extend the overall dynamic range and detection capabilities of the system. The system can employ a laser diode source, a multimode optical fiber sensor, and a CCD camera. The more sensitive detection technique is based on monitoring changes in the speckle pattern due to modal interference.

Certain exemplary embodiments can provide a "smart" bed technology that can non-invasively monitor patient vital signs, motion and overall health in an eldercare setting. The optical fiber sensor can be integrated into the mattress of a bed for continuous, long term monitoring. The results indicate that the integrated sensor can detect patient vital signs such as respiration rate as well as patient movement. Results and analysis are presented.

The continuing shortage of medical staff and the increase in the elder population due to the baby boom after World War II makes the automation of health care an ever increasing priority. In particular, patient monitoring typically is very intrusive and labor intensive. A "smart" bed can non-intrusively monitor patient respiration, heart rate, and movement using spatially distributed integrating fiber optic sensors. Monitoring these three parameters can be helpful important in determining patient condition and preventing future problems for patients in nursing homes and extended care facilities. Measurement of respiration rate and heart rate can provide immediate indication of whether a patient is in any distress, while the measurement of patient movement can be used to determine whether patient movement has been so limited over a period of time that the patient must be turned to a new position by a health care professional to prevent the occurrence or exacerbation of pressure or bed sores.

Theory

The choice of a spatially integrating sensor as opposed to a series of point sensors was made due to the desire for monitoring a non-stationary subject, the patient in the case of eldercare, on a relatively large surface area. Motion on the surface can cause a perturbation of the optical fiber, and locally can modulate the index of refraction and/or the length of the fiber. This modulation can be transduced into a change in the optical signal through the multimode fiber.

Figure 42:
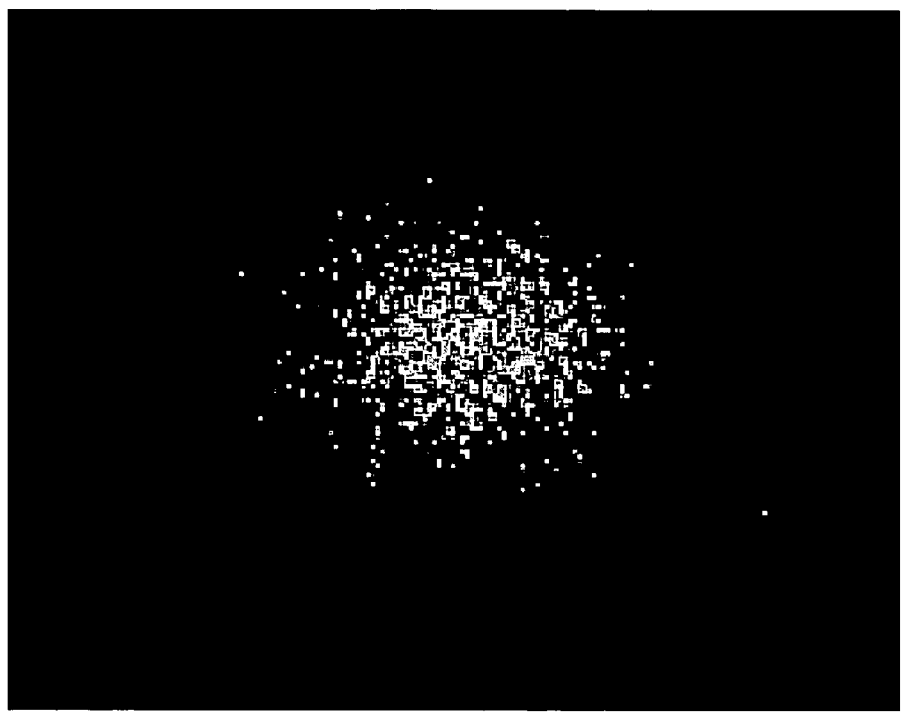
FIG. 42 is an exemplary speckle pattern produced by an exemplary diode laser coupled into 200 micrometer core fiber before pressure was applied.
Figure 43:
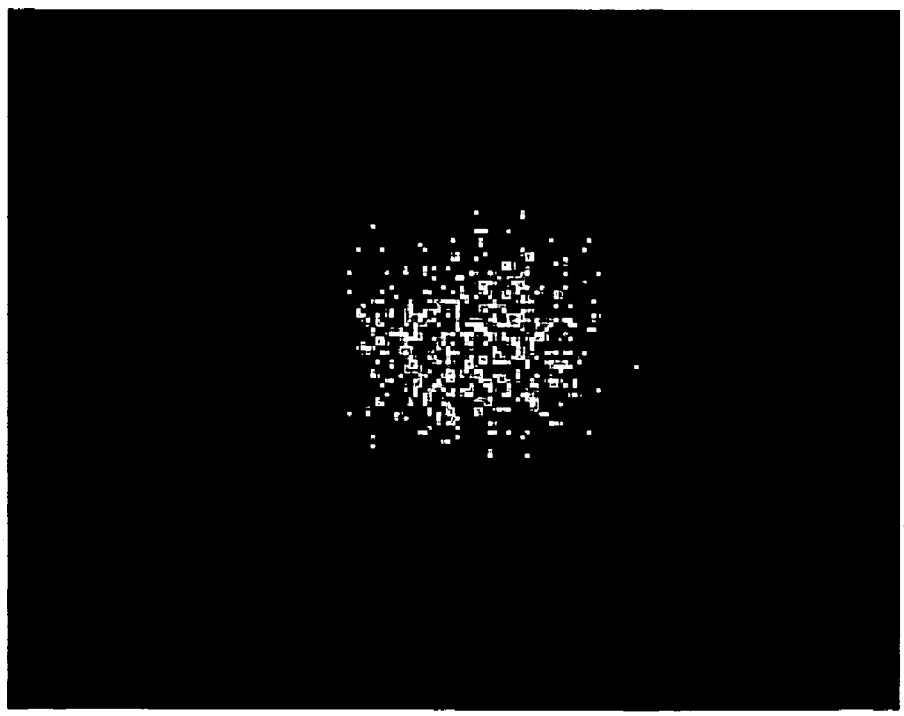
FIG. 43 is an exemplary speckle pattern produced by an exemplary diode laser coupled into 200 micrometer core fiber as pressure was applied, and showing a change in the speckle distribution pattern.

To create the sensor, linearly polarized, coherent light from a laser diode can be coupled into a large core (200 micrometer), step index, multimode optical fiber. In such a case, numerous modes can propagate in the optical fiber. When the output of such a system is incident on a screen. a distinct pattern of speckles can be observed. FIG. 42 shows a typical speckle pattern from such an optical fiber system. It can be shown that the intensity distribution of the speckle pattern is the result of mode self-interaction and mode—mode interaction. The intensity of the $i^{th}$ speckle can be written as:

$$I_i = A_i\{1 + B_i[\cos(\delta_i) - F(t)\phi_i \sin(\delta_i)]\} \quad (1)$$

where $A_i$, $B_i$, $\delta_i$, and $\phi_i$ are constants for any given i. $A_i$ represents a mode self interaction term, $B_i$ accounts for steady state mode—mode interaction, $\delta_i$ is a relative phase term, and $\phi_i$ is a coupling term to the time varying perturbation, F(t). When a perturbation is introduced, the ensemble of speckles in the pattern can act as a series of coupled interferometers subjected to the perturbation simultaneously. Changes in the relative phase between these propagating modes can result in a change in the distribution of the speckle pattern as shown in FIG. 42 and FIG. 43. It should be noted that for small perturbations, the integrated power in the speckle pattern remains constant. In order to recover a signal related to the perturbation, the sum of the absolute value of the change in pixel intensity from frame to frame can be calculated as:

$$I_{SMS}(n) = \sum_{i=1}^{N} |I_i(n) - I_i(n-1)| \quad (2)$$

where N is the total number of pixels, $I_i(n)$ is the intensity of $i^{th}$ pixel in the $n^{th}$ frame. This technique is referred to as statistical mode sensing (SMS) and can produce a signal that is proportional to the absolute value of the first time derivative of the perturbation integrated along the fiber length.

Figure 44:
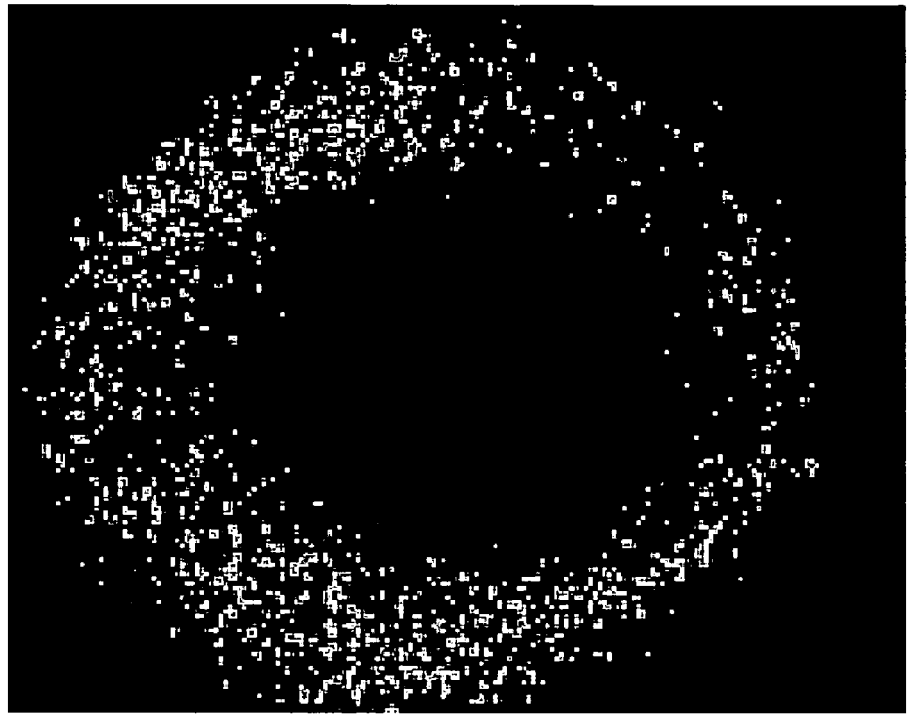
FIG. 44 is an exemplary output pattern spatial distribution of light from an exemplary optical fiber when higher order modes were excited and before pressure was applied to the fiber.
Figure 45:
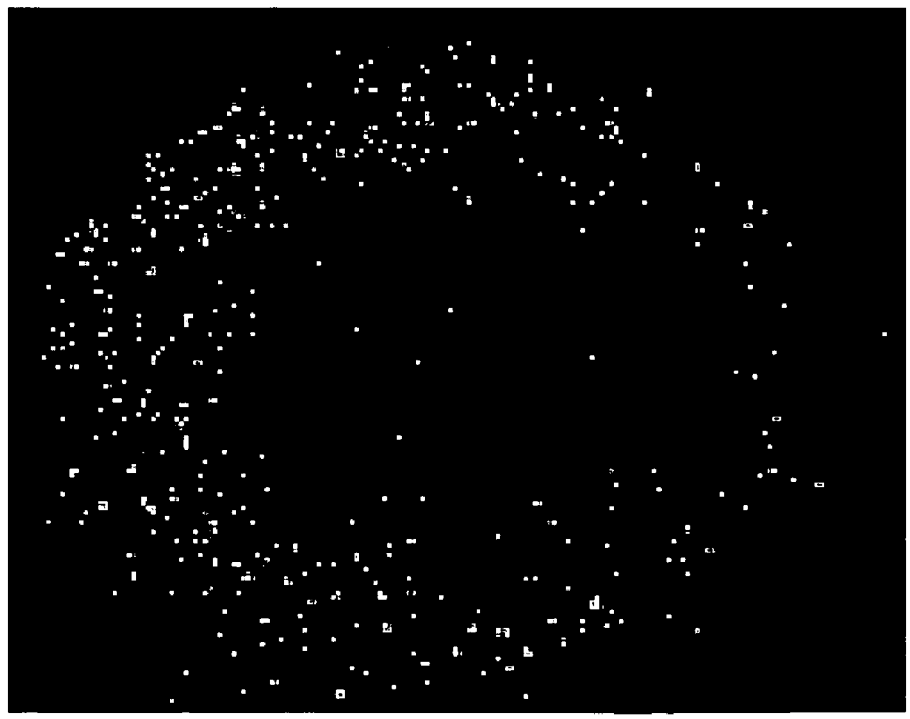
FIG. 45 is an exemplary output pattern spatial distribution of light from an exemplary optical fiber when higher order modes were excited and as pressure was applied to the fiber, and showing how light was coupled to lower order modes and the annular envelope collapsed inward.

The laser diode can be coupled into the higher order modes of the optical fiber and produce an annular envelope on the speckle pattern at the output. Such a pattern is shown in FIG. 44. The absence of light in the center of the output results from an absence of light coupled in the lower order azimuthal modes in the fiber. Larger perturbations of the optical fiber can result in coupling of light from the higher order azimuthal modes to low order azimuthal modes. This can results in a "smearing" of the annular envelope to progressively smaller radii. FIG. 44 and FIG. 45 demonstrate this effect. It has been shown that this effect only becomes evident when relatively large amounts of stress are applied to the optical fiber. Unlike the speckle pattern, the change in the light distribution is due to light coupling to previously unexcited modes in the fiber. Intuitively, this occurs at higher levels of perturbation than the modal interference in the speckle pattern. In this implementation, the change in total intensity inside the annulus can be monitored as:

$$I_{HOME} = \sum_{i=1}^{N} I_i(r < r_{annulus}) \quad (3)$$

where $I_i(r<r_{annulus})$ is the intensity of the $i^{th}$ pixel within the inner radius of the annular ring. This technique is referred to as the higher order mode excitation (HOME) and can produce a signal that is proportional to the value of the perturbation.

Thus, light incident in a predetermined central area of a photodetector can be indicative of a coupling of light from the higher order azimuthal modes to low order azimuthal modes, which can be indicative of a perturbation of a predetermined magnitude. Conversely, if light is applied to lower order azimuthal modes of a fiber, a perturbation of a predetermined magnitude can cause coupling of the light from the lower order modes to higher order modes, and thereby can cause a "smearing" of a circular envelope to progressively larger radii and/or light to begin being incident in a predetermined annular region of a photodetector, such as a pixelated photodetector. Such incident light and/or the causative perturbations can be detected, logged, characterized, and/or monitored, etc.

Figure 46:
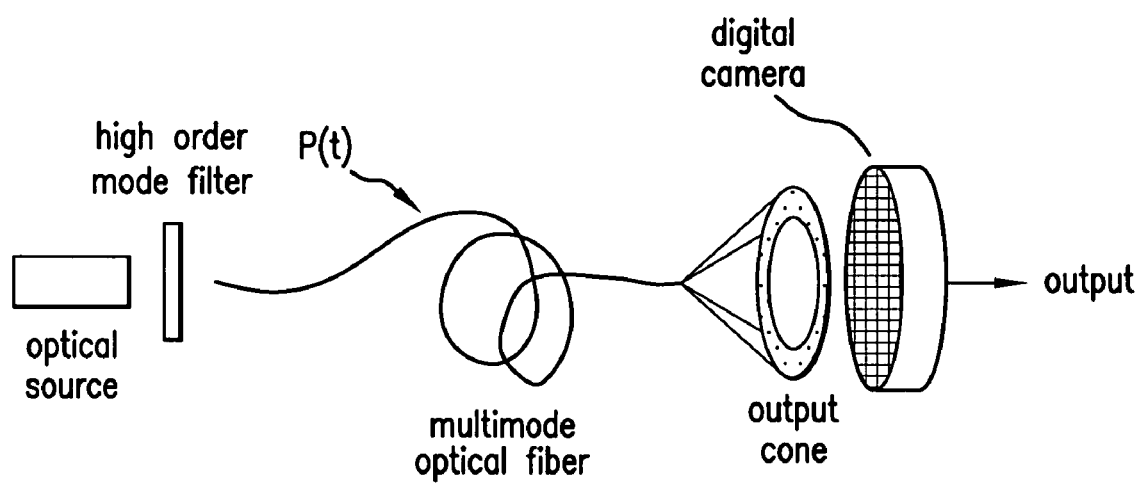
FIG. 46 is a block diagram of an exemplary embodiment of a system comprising both an exemplary statistical mode (STM) sensor and a high order mode excitation (HOME) sensor.

Combining these two distinct detection methods, modal interference and high to low order modal coupling, can extend the dynamic range of the optical sensor system. A schematic diagram of this technique is shown in FIG. 46. When the fiber is perturbed, the perturbation can couple light from the higher order modes to lower order modes as well as change the distribution of the laser speckle pattern. The SMS technique can be sensitive to relatively small perturbations and the HOME technique can be sensitive to relatively large perturbations.

The experimental implementation of this system utilized a low power laser diode at 670 nanometers as the source. Coupling of the light into the higher order modes can be accomplished via a number of different methods. For high coupling efficiency, the laser light can be expanded and collimated. This collimated beam then can be spatially filtered by placing an opaque obscuration in the center of the beam. Finally, the annular beam can be focused into the optical fiber at numerical aperture within the acceptable input for the chosen fiber. Alternatively, the light directly out of the laser can be coupled into the optical fiber at an angle. The latter method was chosen due to ease of implementation and an abundance of optical power. The optical fiber utilized was a commercially available 200 micrometer core silica multimode fiber with an NA of 0.49. The excitation angle between the laser and the optical fiber was in the 10 degree to 20 degree range depending on the length and placement of the optical fiber transducer. For experiments with patients laying on a bed, the optical fiber can be placed either on top of the mattress or between the mattress and the metal, spring support. The latter method can provide a large number of high stress points where the fiber crosses the metal supports. The former method can put the fiber in more direct contact with the patient, but does not necessarily provide high stress points. For the experiments performed in this work, the optical fiber was placed on top of the mattress due to background signal saturation of the HOME technique due to the high stress areas when in contact with the bed frame. Approximately 2 meters of fiber were used as the transducer. This fiber was run across the width of the bed and back. and included four points where it crossed over itself. The fiber was placed approximately where the patient's chest contacted the bed. The output of the optical fiber was directly incident on a 256×256 pixel camera. The frame rate of the camera was set at 20 Hz and the integration time set at 170 microseconds. Data was stored in a buffer on the camera and accessed by computer after acquisition of a full data set. All data processing was done in the MATLAB programming environment.

Results

Figure 47:
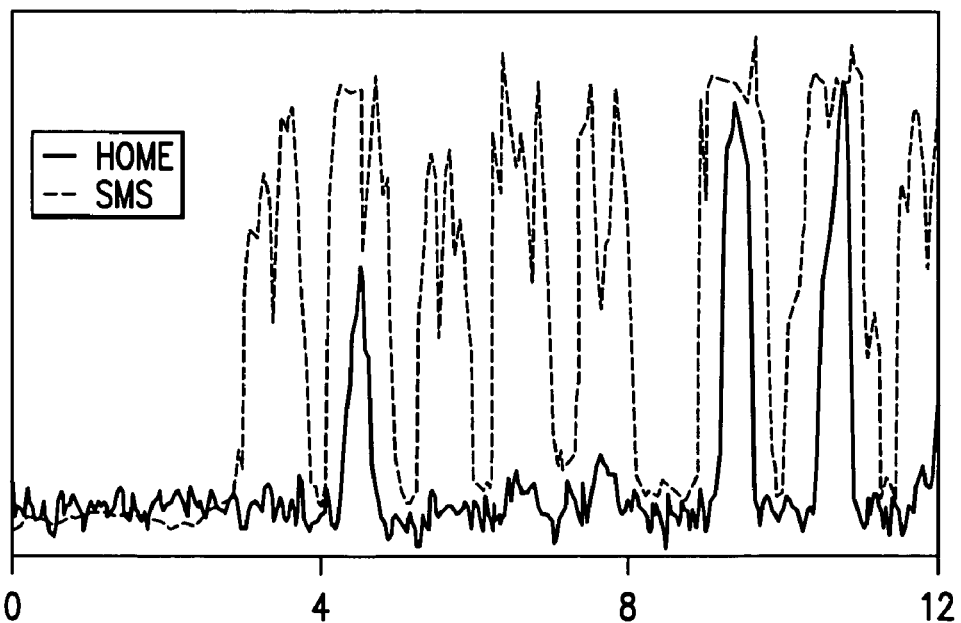
FIG. 47 is a plot of normalized exemplary normalized signals vs. time (seconds) from exemplary SMS and exemplary HOME sensing techniques, and showing that the HOME signal only responds after the SMS signa! has saturated and that the SMS signal dips as the HOME signal increases due to light coupling out of the annular pattern and into the center area.
Figure 48:
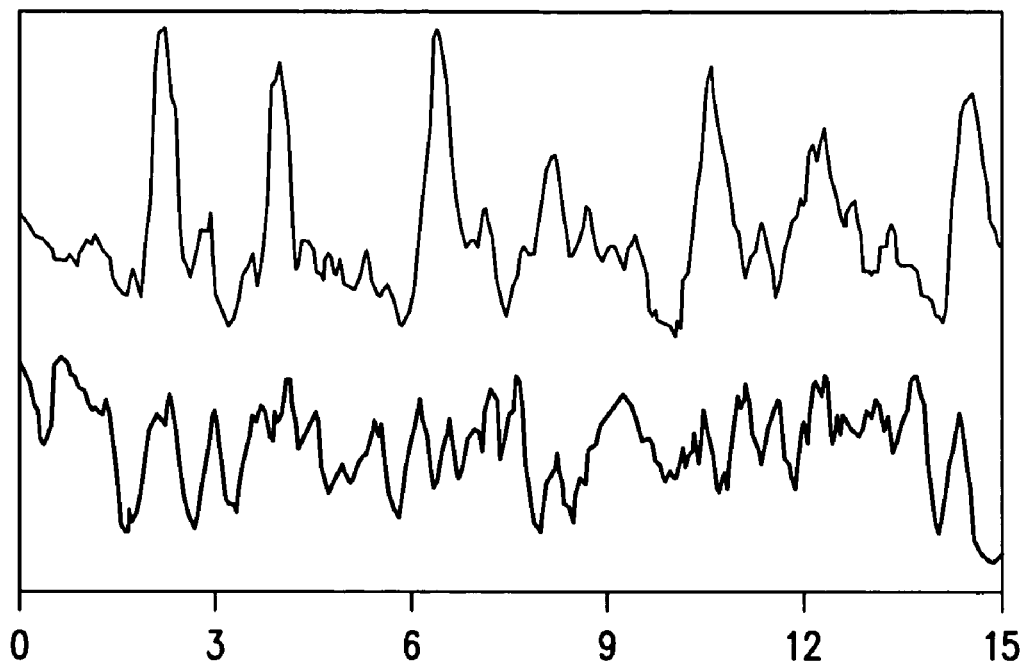
FIG. 48 is a plot of normalized exemplary SMS (top) and exemplary HOME (bottom) signals vs. time (seconds) taken for 15 seconds with a patient breathing at approximately 15 breaths per minute, and showing that the SMS signal clearly shows both inhale and exhale cycles, and that the HOME data is uncorrelated to breathing rate.

Initial data was taken to confirm the relative sensitivity of the two techniques. Laser light was coupled into two meters of optical fiber that was coiled on an optical bench. The fiber then was periodically compressed to produce a signal. FIG. 47 shows the SMS and HOME signal from this experiment. As anticipated, the SMS signal registered smaller perturbations applied to the fiber. As the SMS signal saturated, the HOME sensor registered the signal strength of the larger perturbations. Following this confirmation of sensor operation, the optical fiber was placed on a mattress as described supra. FIG. 48 shows SMS and HOME data for a patient on the bed breathing at approximately 15 breaths per minute. The data demonstrate the ability of the system to sense the small perturbations from respiration through the SMS technique without affecting the HOME signal.

Figure 49:
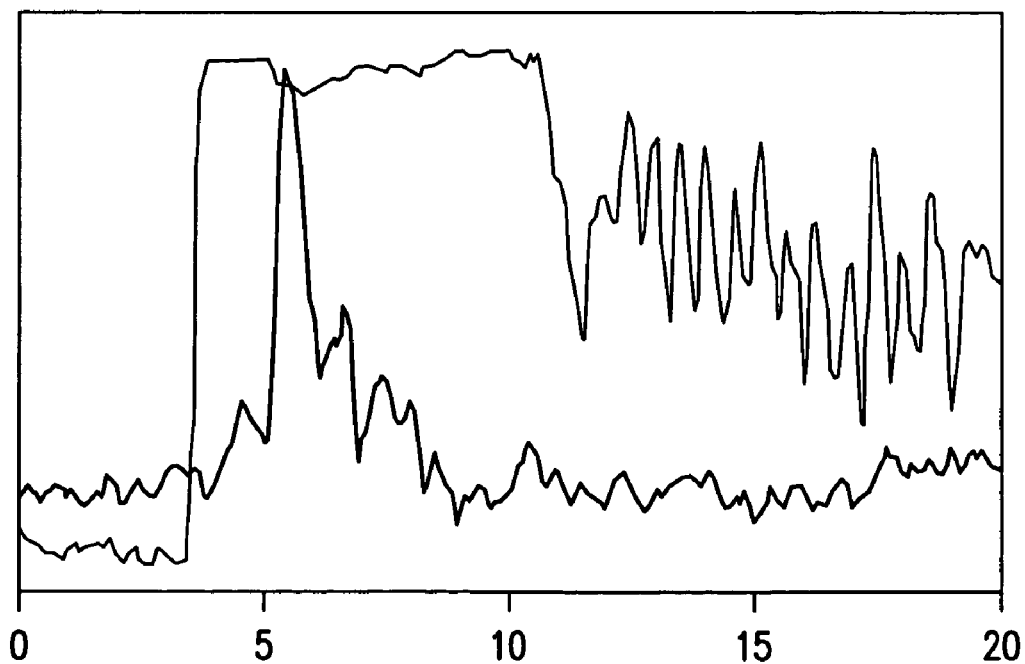
FIG. 49 is a plot of normalized exemplary SMS (gray) and exemplary HOME (black) signals vs. time (seconds) taken for 20 seconds as a patient enters a bed and breaths at approximately 15 breaths per minute, and showing that the SMS signal initially saturated then clearly showed both inhale and exhale cycles, and that the HOME signal registered the gross motion of the patient getting into the bed.

The data in FIG. 49 shows SMS and HOME signals for a patient getting into the bed and then breathing at approximately 30 breaths per minute. Again, the SMS signal detects the small perturbation due to respiration, However large motions such as getting into bed and shifting on the bed saturate the SMS signal. These motions are detected by the HOME technique. Thus, the overall system's dynamic range is increased through the utilization of two sensing techniques employed on a single sensing platform.

Figure 50:
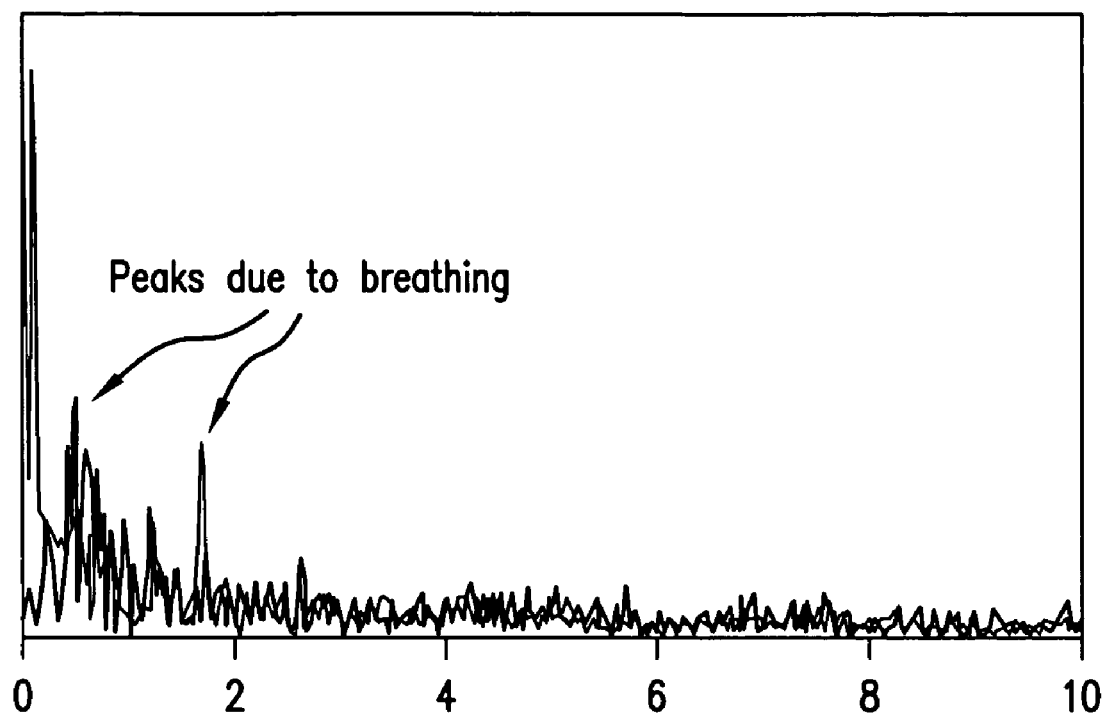
FIG. 50 is a plot of power density (arbitrary units) vs. frequency (Hz) for exemplary data from a fast Fourier transform of exemplary temporal data with a patient breathing at 15 (black) and 30 (gray) breaths per minute.

The data in FIG. 50 shows the spectral power distribution of the temporal signals recorded in FIG. 48 and FIG. 49. The respiration rates appear at twice the respiration frequency due to the fact that the signal is proportional to the absolute value of the first time derivative of the perturbation.

Discussion

As can be seen from these results, the combination of STM and HOME techniques can be used to detect patient respiration and movement. By the nature of its transduction process, the SMS technique does not become saturated by a DC signal from time independent pressure on the optical fiber. As long as the system is in operation, the speckle pattern will always be present and will always change in response to additional time dependent perturbations. Thus, the size of the DC component does not affect the sensitivity of this signal processing method. However, the technique is very sensitive to small perturbations applied to the fiber. Saturation of the signal occurs as the speckle pattern changes very rapidly due to the perturbation. For this application, the signal is also somewhat independent of patient weight. On the other hand, the HOME technique can be saturated by time independent perturbations large enough to cause the available propagating mode volume to become completely filled. However, the transduction process is significantly less sensitive to perturbation than the SMS technique. Thus, proper optical fiber layout can result in the HOME technique having sensitivity to signals that saturate the SMS technique. It is for this reason that the bare optical fiber used in this work was placed on top of the fiber. When the optical fiber was placed between the mattress and the metal bed frame, the patient's weight produced a DC signal that saturated the HOME technique. This sensing platform offers the potential to be low cost, personal computer-compatible, and have the capability to be integrated into larger wireless monitoring systems.

Certain exemplary embodiments employ a cost effective wireless version of the SMS sensor and/or the HOME sensor. In this case, the optical detector can be an off-the-shelf digital camera with the capability of wireless transmission to a remote wireless receiver coupled to a personal computer. Certain exemplary embodiment primarily use off-the-shelf components. The system can include a laptop PC, a wireless receiver, a wireless transmitter containing a laser diode and a wireless digital camera that served as the detector, and a sensing fiber. The camera can transmit image data from the sensing location to the laptop PC where the individual pixels from sequential frames can be processed to provide the appropriate output. This particular configuration can allow the sensor and processing to be separated with the potential for a single PC to be able to multiplex and process the outputs from a number of spatially separated sensors simultaneously which can result in a significant reduction in the cost per sensing location due to the fact that the laptop PC can be the most expensive component in the whole system. This system can be modified to perform dual mode sensing.

In certain embodiments, parameters such as fiber coatings, fiber backing material, and/or fiber length can be varied to create sensors for numerous applications. Although the emphasis of this research has been on eldercare monitoring, the flexibility introduced by both the choice of sensing element as well as the ability to spatially tailor the layout of a distributed sensing element allows application to such fields as intruder detection, structural health monitoring, seismic monitoring, and/or active control systems. The simplicity of the sensing platform and the ability to transmit data wirelessly also make this system amenable to rapid field deployment.

Thus, certain exemplary embodiments comprise a system comprising a spatially distributed multimode optical fiber; a pixelated photodetector configured to detect a plurality of optical signals provided from said fiber, a first portion of the optical signals indicative of modal conversion and a second portion of the optical signals indicative of modal interference, a predetermined area of said pixelated photodetector adapted to be illuminated by the first portion of the optical signals; and a signal processing module adapted to decode and interpret a plurality of detected variables related to the optical signals.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of the appended claims. For example, regardless of the content of any portion (e.g., title, field, background, summary, abstract, drawing figure, etc.) of this application, unless clearly specified to the contrary, there is no requirement for the inclusion in any claim of the application of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all subranges therein. Any information in any material (e.g., a United States patent, United States patent application, book, article, etc.) that has been incorporated by reference herein, is only incorporated by reference to the extent that no conflict exists between such information and the other statements and drawings set forth herein. In the event of such conflict, including a conflict that would render a claim invalid, then any such conflicting information in such incorporated by reference material is specifically not incorporated by reference herein.

What is claimed is:

1. A system, comprising:
   a spatially distributed multimode optical fiber;
   a pixelated photodetector configured to detect a plurality of optical signals provided from said fiber, the optical signals related to perturbations applied to said optical fiber, a first portion of the optical signals indicative of modal conversion and a second portion of the optical signals indicative of modal interference, a predetermined central area of said pixelated photodetector adapted to be illuminated only by the first portion of the optical signals; and
   a signal processing module adapted to decode and interpret a plurality of detected variables related to the optical signals.

2. The system of claim 1, further comprising a coherent optical source optically couplable to said optical fiber.

3. The system of claim 1, further comprising a laser diode optically couplable to said optical fiber.

4. The system of claim 1, further comprising a laser light pointer optically couplable to said fiber.

5. The system of claim 1, further comprising an electronic driver adapted to control light provided to said fiber.

6. The system of claim 1, wherein said fiber is integrating.

7. The system of claim 1, wherein said fiber is spatially distributed with respect to a patient bed for optimized detection of patient movement.

8. The system of claim 1, wherein said fiber is spatially distributed with respect to a patient bed for optimized detection of patient respiration.

9. The system of claim 1, wherein said fiber is spatially distributed with respect to a patient bed for optimized detection of patient heart rate.

10. The system of claim 1, wherein said fiber is spatially distributed with respect to a patient bed for optimized detection of any combination of patient movement, respiration rate, and heart rate.

11. The system of claim 1, wherein said fiber is adapted to provide modal conversion.

12. The system of claim 1, wherein said fiber is adapted to provide inter-modal interference.

13. The system of claim 1, wherein the optical signals comprise a speckle pattern.

14. The system of claim 1, further comprising a matched spatial filter adapted to spatially filter light provided to said fiber.

15. The system of claim 1, further comprising a matched spatial filter adapted to filter the optical signals.

16. The system of claim 1, further comprising a matched spatial filter adapted to spatially filter the plurality of detected variables of the optical signals.

17. The system of claim 1, further comprising a matched spatial filter adapted to filter a plurality of digitized images provided by said photodetector.

18. The system of claim 1, wherein said photodetector is optically couplable to said optical fiber.

19. The system of claim 1, wherein said photodetector provides an output proportional an integrated perturbation along said fiber.

20. The system of claim 1, further comprising a wireless digital module coupled to said photodetector and adapted to wirelessly transmit a wireless signal encoding the plurality of detected variables of the optical signals.

21. The system of claim 1, further comprising a wireless digital module coupled to said photodetector and adapted to wirelessly transmit a wireless signal encoding a plurality of digitized images of the optical signals.

22. The system of claim 1, further comprising a wireless receiver adapted to receive a wireless signal encoding the plurality of detected variables of the optical signals.

23. The system of claim 1, further comprising a wireless receiver adapted to receive a wireless signal encoding the plurality of detected variables of the optical signals, said wireless receiver coupled to said signal processing module.

24. The system of claim 1, wherein said signal processing module is adapted to decode a plurality of digitized images and to interpret one or more variables of the plurality of digitized images, the plurality of digitized images related to the optical signals.

25. The system of claim 1, wherein said signal processing module is adapted to provide an output proportional to an absolute value of $\Delta P/\Delta t$, where P is an integrated perturbation along said optical fiber and t is time.

26. The system of claim 1, wherein said signal processing module is adapted to provide matched spatial filtering of a plurality of digitized images to optimize a signal-to-noise ratio, the plurality of digitized images related to the optical signals.

27. The system of claim 1, wherein said signal processing module is adapted to process a predetermined portion of the optical signals.

28. The system of claim 1, wherein said signal processing module is adapted to process a portion of the optical signals, the portion associated with a human vital sign.

29. The system of claim 1, wherein said signal processing module is adapted to interpret a frequency of a perturbation of the fiber.

30. The system of claim 1, wherein said signal processing module is adapted to interpret a frequency of a perturbation of the plurality of detected variables.

31. The system of claim 1, wherein said signal processing module is adapted to interpret fluctuations in a speckle pattern of the optical signals.

32. The system of claim 1, wherein said signal processing module is adapted to interpret a portion of the plurality of detected variables associated with the first portion of the optical signals.

33. The system of claim 1, wherein said signal processing module is adapted to interpret a portion of the plurality of detected variables associated with the second portion of the optical signals.

34. The system of claim 1, wherein said signal processing module is adapted to interpret a frequency of at least a portion of the perturbations, the interpreted frequency corresponding to a patient vital sign.

35. The system of claim 1, wherein said signal processing module is adapted to interpret a frequency of at least a portion of the perturbations, the interpreted frequency corresponding to a patient movement.

36. The system of claim 1, wherein said signal processing module is adapted to monitor the plurality of detected variables for a change in a patient's vital sign.

37. The system of claim 1, wherein said signal processing module is adapted to monitor the plurality of detected variables for a change in a patient's movement.

38. The system of claim 1, wherein said signal processing module is adapted to automatically monitor the plurality of detected variables for a change in patient movement, respiration rate, or pulse rate.

39. The system of claim 1, wherein said system comprises an STM sensor and a HOME sensor.

40. A method, comprising:
transmitting from a wireless digital pixelated photodetector coupled to a spatially distributed multimode optical fiber a signal encoding a plurality of detected variables of optical signals emerging from the optical fiber, a first portion of the optical signals related to a first plurality of perturbations applied to the optical fiber, indicative of modal conversion, and illuminating only a predetermined central area of the photodetector, and a second portion of the optical signals related to a second plurality of perturbations applied to the optical fiber, indicative of modal interference, and illuminating other than the predetermined central area of the photodetector;
receiving the signal at a wireless receiver;
decoding the signal at a signal processing module coupled to the wireless receiver; and
interpreting the plurality of detected variables of the decoded signal.

41. A method, comprising:
spatially distributing a multimode optical fiber in a predetermined pattern for facilitating sensing of a predetermined type of perturbation;
transmitting optical signals from the spatially distributed integrating multimode optical fiber;
detecting the optical signals at a pixelated photodetector, the optical signals related to perturbations applied to the optical fiber, a first portion of the optical signals indicative of modal conversion and a second portion of the optical signals indicative of modal interference, a predetermined central area of said pixelated photodetector adapted to be illuminated only by the first portion of the optical signals; and
transmitting a wireless signal encoding a plurality of detected variables of the optical signals.

42. A machine-readable medium comprising instructions for activities comprising:
decoding a wireless signal obtained from a wireless digital pixelated photodetector coupled to an optical fiber spatially distributed in a predetermined pattern for facilitating sensing of a predetermined type of perturbation, the wireless signal encoding a plurality of detected variables of optical signals emerging from the spatially distributed optical fiber, a first portion of the optical signals related to a first plurality of perturbations applied to the optical fiber, indicative of modal conversion, and illuminating only a predetermined central area of the photodetector, and a second portion of the optical signals related to a second plurality of perturbations applied to the optical fiber, indicative of modal interference, and illuminating other than the predetermined central area of the photodetector; and interpreting the plurality of detected variables of the decoded signal.

* * * * *